(12) United States Patent
Yokoyama et al.

(10) Patent No.: US 8,846,012 B2
(45) Date of Patent: Sep. 30, 2014

(54) MELANIN PRODUCTION INHIBITOR

(75) Inventors: Kouji Yokoyama, Yokohama (JP); Makoto Kimura, Yokohama (JP); Masashi Tamai, Yokohama (JP); Yuko Saitoh, Yokohama (JP); Tomomi Kato, Yokohama (JP); Yu Ikeda, Yokohama (JP)

(73) Assignee: Pola Chemical Industries Inc., Shizuoka (JP)

( * ) Notice: Subject to any disclaimer, the term of this patent is extended or adjusted under 35 U.S.C. 154(b) by 443 days.

(21) Appl. No.: 13/131,827

(22) PCT Filed: Dec. 22, 2009

(86) PCT No.: PCT/JP2009/071279
§ 371 (c)(1),
(2), (4) Date: May 27, 2011

(87) PCT Pub. No.: WO2010/074052
PCT Pub. Date: Jul. 1, 2010

(65) Prior Publication Data
US 2011/0243865 A1 Oct. 6, 2011

(30) Foreign Application Priority Data

Dec. 22, 2008 (JP) ................................. 2008-325969

(51) Int. Cl.
| | | |
|---|---|---|
| *A61K 8/49* | (2006.01) | |
| *C07D 233/58* | (2006.01) | |
| *C07D 401/06* | (2006.01) | |
| *A61K 8/44* | (2006.01) | |
| *A61K 8/41* | (2006.01) | |
| *A61K 8/34* | (2006.01) | |
| *C07D 207/404* | (2006.01) | |
| *A61Q 19/02* | (2006.01) | |
| *C07D 213/38* | (2006.01) | |
| *C07D 213/30* | (2006.01) | |
| *C07D 295/03* | (2006.01) | |
| *C07D 207/12* | (2006.01) | |
| *C07D 295/096* | (2006.01) | |

(52) U.S. Cl.
CPC ............ *C07D 233/58* (2013.01); *A61K 8/4913* (2013.01); *A61K 8/494* (2013.01); *A61K 8/418* (2013.01); *A61K 8/34* (2013.01); *C07D 207/404* (2013.01); *A61Q 19/02* (2013.01); *C07D 401/06* (2013.01); *A61K 8/49* (2013.01); *A61K 8/4946* (2013.01); *C07D 213/38* (2013.01); *C07D 213/30* (2013.01); *A61K 8/411* (2013.01); *C07D 295/03* (2013.01); *C07D 207/12* (2013.01); *C07D 295/096* (2013.01); *A61K 8/41* (2013.01); *A61K 8/4926* (2013.01); *A61K 8/44* (2013.01)
USPC ....... 424/62; 548/344.1; 548/545; 546/272.7; 546/316

(58) Field of Classification Search
USPC ........ 424/62; 548/344.1, 545; 546/272.7, 316
See application file for complete search history.

(56) References Cited

U.S. PATENT DOCUMENTS

| | | | | |
|---|---|---|---|---|
| 3,577,413 | A | * | 5/1971 | Adams et al. .................. 544/178 |
| 3,629,273 | A | | 12/1971 | Draber et al. |
| 4,472,421 | A | | 9/1984 | Buchel et al. |
| 2004/0127464 | A1 | | 7/2004 | Brugnara et al. |

FOREIGN PATENT DOCUMENTS

| | | |
|---|---|---|
| BE | 901016 A1 | 3/1985 |
| CN | 1394685 A | 2/2003 |
| CN | 1989143 A | 6/2007 |
| CN | 101096359 A | 1/2008 |

(Continued)

OTHER PUBLICATIONS

Takeda, et al. (supervised) "Effectiveness of Cosmetic Products," Yakuji-nippohsha, pp. 144-159, 2001.

(Continued)

*Primary Examiner* — Anoop Singh
*Assistant Examiner* — Anna Falkowitz
(74) *Attorney, Agent, or Firm* — Knobbe, Martens, Olson & Bear LLP

(57) ABSTRACT

Disclosed is a melanin production inhibitor which has an excellent inhibitory activity on the production of melanin and is highly safe. The melanin production inhibitor is represented by general formula (1) (excluding clotrimazole) and/or a pharmacologically acceptable salt thereof. In the formula, A1, A2 and A3 are independently selected from a hydrogen atom, an aryl group which may have a substituent, and an aromatic heterocyclic group which may have a substituent. At least one of A1, A2 and A3 is selected from the aryl group and the aromatic heterocyclic group, the total number of carbon atoms contained in A1, A2 and A3 is 6 to 50 and, when at least two of A1, A2 and A3 represent the aryl groups or the aromatic heterocyclic groups, the adjacent two aryl or aromatic heterocyclic groups may be bound to each other via an alkyl chain or an alkenyl chain to form a ring; m represents an integer of 0 to 2; X represents a hetero atom, a hydrogen atom, or a carbon atom; R1 and R2 are independently selected from a hydrogen atom and an oxo group. When one of R1 and R2 is an oxo group, the other is not present. R3 is selected from a hydrogen atom, and a $C_{1-8}$ hydrocarbon group in which one or some of hydrogen atoms or carbon atoms may be substituted by a hetero atom or hetero atoms. The number of R3's present in the compound corresponds to X and, when two or more R3's are present, the R3's are independently present and the adjacent two R3's may be bound to each other to form, together with X, a ring, and the terminal of R3 may be bound to a carbon atom to which A1, A2 and A3 are bound, thereby forming a ring.

2 Claims, No Drawings

(56) References Cited

FOREIGN PATENT DOCUMENTS

| CN | 101256147 A | 9/2008 | | |
|---|---|---|---|---|
| EP | 0599220 A1 | 6/1994 | | |
| FR | 1540727 A | 9/1968 | | |
| GB | 1184237 A | 3/1970 | | |
| JP | 08-231367 | 9/1996 | | |
| JP | 08-231367 A | 9/1996 | | |
| JP | 09-255634 | 9/1997 | | |
| JP | 09-255634 A | 9/1997 | | |
| JP | 2004-067515 | 3/2004 | | |
| JP | 2004-067515 A | 3/2004 | | |
| JP | 2-4-067515 | * 4/2004 | ........... | A61K 31/216 |
| KR | 10-2004-0007044 | 1/2004 | | |
| KR | 10-0511114 B1 | 8/2005 | | |
| WO | WO 01/49663 A2 | 7/2001 | | |
| WO | WO 02/060404 | 8/2002 | | |
| WO | WO 03/039550 | 5/2003 | | |
| WO | WO 2005/118598 A1 | 12/2005 | | |
| WO | WO 2007/097931 A2 | 8/2007 | | |

OTHER PUBLICATIONS

Ohmori, Fragrance Journal, No. 14, pp. 118-126, 1995.
Green, A Wily-Interscience Publication, pp. 173-176 and 273-274, 1981.
Izumiya, et al. "Basis and Experiments of Peptide Synthesis," Maruzen Kabushikigaisha, pp. 38-39, 1985.
Ogo, et al. "Synthesis and Biological Evaluation of L-cysteine Derivatives as Mitotic Kinesin Eg5 Inhibitors," *Bioorganic & Medicinal Chemistry Letters* 17, pp. 3921-3924, 2007.
Sasse, et al. "(Partial) Agonist/Antagonist Properties of Novel Diarylalkyl Carbamates on Histamine $H_3$ Receptors," *Bioorganic & Medicinal Chemistry* 8, No. 5, pp. 1139-1149, 2000.
Dutta, et al. "Rational Design and Synthesis of Novel 2,5-Disubstituted *cis*-and *trans*-Piperidine Derivatives Exhibiting Differential Activity for the Dopamine Transporter," *Bioorganic & Medicinal Chemistry Letters* 11, pp. 2337-2340, 2001.
Shanklin, et al. "Synthesis, Calcium-Channel-Blocking Activity, and Antihypertensive Activity of 4-(Diarylmethyl)-1-[3-(aryloxy)propyl]piperidines and Structurally Related Compounds," *J. Med. Chem.*, vol. 34, No. 10, pp. 3011-3022, 1991.
International Search Report issued on Jan. 26, 2010 to international application No. PCTJP2009/071279.
Greene, "Protective Groups in Organic Synthesis," A Wiley-Interscience Publication, pp. 173-176 and 273-274 (1981).
Takeda et al. (supervised), "Effectiveness of Cosmetic Products," Yakuji-nippohsha, pp. 144-159 (2001).

Office Action issued in corresponding Russian Application No. 2011130514 on Oct. 8, 2013.
Extended European search report issued in corresponding European Patent Application No. 09834853.5, dated Mar. 6, 2014.
Bartroli et al., "Synthesis and Antifungal Activity of a Series of Difluorotritylimidazoles," *Arzneimittel-Forschung/Drug Research*, ECV Editio Cantor Verlag, Aulenoorf, Germany, vol. 42 (I)(6), pp. 832-835 (1992).
Griffiths, "The Metabolism of N-Triphenyimethylmorpholine in the Dog and Rat," *Biochemical Journal*, vol. 108, pp. 731-740 (1968).
Walker, "A Convenient Preparation of Thioethers from Alcohols," *Tetrahedron Letters*, Pregamon Press, Great Britain, No. 51, pp. 4475-4478 (1977).
Office Action issued in corresponding Chinese Patent Application No. 200980151797.2, on May 21, 2014.
Office Action issued in corresponding Ukrainian Patent Application No. 2011 09121, on May 23, 2014.
Maltese, "Reductive Demercuration in Deprotection of Trityl Thioethers, Trityl Amines, and Trityl Ethers," *J. Org. Chem.*, vol. 66, pp. 7615-7625 (2001).
Meier et al., "Trends in Chemical Shift Dispersion in Fullerene Derivatives, Local Strain Affects the Magnetic Environment of Distant Fullerene Carbons," *J. Org. Chem.*, vol. 68, pp. 7867-7870 (2003).
Miyake et al., "Solvolysis of Benzyl Alcohols and Ethers in 1,2-Diols and Application to a Deprotection of Benzyl Ether-type Protecting Groups," *Chemistry Letters*, vol. 35(7), pp. 778-779 (2006).
PubChem Compound, http://pubchem.ncbi.nlm.nih.gov/summary/summary.cgi?sid=173552266&viewopt=Pubchem#x400, downloaded Jun. 24, 2014, in 4 pages.
PubChem Substance, http://pubchem.ncbi.nlm.nih.gov/summary/summary.cgi?sid=4921433&loc=esrss, downloaded Jun. 24, 2014, in 2 pages.
Saidi et al., "Aminoalkylation with Aldehydes Mediated by Solid Lithium Perchlorate," *Monatshefte fur Chemie*, vol. 135, pp. 309-312 (2004).
Soroka et al., "Tritylamine (triphenylmethylamine) in organic synthesis; II. The reaction of tritylamine with oxiranes—synthesis of N-trityl-β-aminoalcohols," *ARKIVOC*, vol. 7, pp. 31-37 (2003).
Tomashenko et al., "Synthesis of Tertiary sec-Alkylamines by the Addition of Grignard Reagents to N,N-Dialkylformamides Mediated by $Ti(OiPr)_4$ and $Me_3SiCl$," *Eur. J. Org. Chem.*, pp. 5107-5111 (2008).
Wang et al., "Pharmacological properties of hydrophilic and lipophilic derivatives of octreotate," *Nuclear Medicine and Biology*, vol. 31, pp. 21-30 (2004).

* cited by examiner

US 8,846,012 B2

MELANIN PRODUCTION INHIBITOR

CROSS-REFERENCE TO RELATED APPLICATIONS

This application is the U.S. National Phase under 35 U.S.C. §371 of International Application PCT/JP2009/071279, filed Dec. 22, 2009, which was published in a non-English language, which claims priority to JP Application No. 2008-325969, filed Dec. 22, 2008.

TECHNICAL FIELD

The present invention relates to a melanin production inhibitor, and an external preparation for skin which includes the same, such as a cosmetic.

BACKGROUND ART

Prevention and amelioration of skin symptoms such as age spots, freckles, and pigmentation, which are caused by factors such as increasing age, stress, and ultraviolet rays, are very important concerns especially for women.

In order to respond to such concerns, a variety of skin-whitening agents have been developed heretofore. For example, skin-whitening agents each including ascorbates, hydrogen peroxide, colloidal sulfur, glutathione, hydroquinone, or catechol have been developed (for example, see Non Patent Document 1 and Non Patent Document 2).

However, it is known that any of the skin-whitening agents are not effective for some symptoms. However, the reasons are not known in detail. Further, some of the skin-whitening agents are shown to have safety problems.

In addition, miconazole and clotrimazole, which are known as antimycotics, have been reported to have tyrosinase inhibitory activities (Patent Documents 2 and 3). However, miconazole and clotrimazole each have a high antimycotic activity, and hence it is problematic in safety to use the compounds in an external preparation for skin such as a cosmetic.

In this context, development of a novel skin-whitening agent which has an excellent skin-whitening effect and is highly safe has been desired.

On the other hand, a sterically-bulky aromatic group (in particular, a diphenylmethyl group or a triphenylmethyl group) or an aromatic heterocyclic group is widely known as an effective protective group for a hydroxyl group or an amino group in synthesis of an organic low-molecular-weight compound, a peptide, and a nucleic acid (for example, see Non Patent Document 3 and Non Patent Document 4). An intermediate compound obtained by using such protective group (for example, see Non Patent Document 5 and Non Patent Document 6) is applied to organic syntheses on a wide range of scales from a laboratory scale to an industrial scale.

Further, it has been reported that some of compounds each having a chemical structure including a sterically-bulky substituent such as a substituted diphenylmethyl group or triphenylmethyl group have biological activities such as an anti-tumor activity (for example, see Non Patent Document 5), an antimycotic effect (for example, see Patent Document 1), an antihistaminic effect (for example, see Non Patent Document 6), a dopamine uptake inhibitory effect (for example, see Non Patent Document 7), and a calcium antagonistic effect (for example, see Non Patent Document 8).
[Patent Document 1] JP 09-255634 A
[Patent Document 2] WO 02/060404 A1
[Patent Document 3] KR 10-2004-0007044 A
[Non Patent Document 1] Edited by Katsuyuki Takeda et. al., "Utility, Evaluation Technology and Future Perspective of Cosmetics", published by YAKUJI NIPPO LIMITED. (2001)
[Non Patent Document 2] Yoshiyuki Ohmori, FRAGRANCE JOURNAL, extra edition, No. 14, 1995, 118-126
[Non Patent Document 3] Theodora W. Green, Protective Groups in Organic Synthesis, A Wiley-Interscience Publication.: 1981, P 173-176 and P 273-274
[Non Patent Document 4] Nobuo Izumiya, Tetsuo Kato, Haruhiko Aoyagi, Michinori Waki, Basic and Experiment of Peptide Synthesis: MARUZEN Co., Ltd., 1985, P 38
[Non Patent Document 5] Naohisa Ogo et. al., Bioorganic & Medicinal Chemistry, 17(14), 3921-3924 (2007)
[Non Patent Document 6] Sasse A., et. al., Bioorganic & Medicinal Chemistry, 8(5), 1139-1149 (2000)
[Non Patent Document 7] Dutta A K. et. al., Bioorganic & Medicinal Chemistry, 11(17), 2337-2340 (2001)
[Non Patent Document 8] Shanklin J R Jr., et al., J. Med. Chem., 34(10), 3011-3022 (1991)

SUMMARY OF INVENTION

Technical Problem

An object of the present invention is to provide a novel melanin production inhibitor. Another object of the present invention is to provide a melanin production inhibitor which has an excellent inhibitory effect on melanin production and is highly safe. Still another object of the present invention is to provide an external preparation for skin which has an excellent inhibitory effect on melanin production and is highly safe.

Solution to Problem

The inventors of the present invention have found out that, of compounds each having a chemical structure including a sterically-bulky substituent such as a substituted diphenylmethyl group or triphenylmethyl group, specific compound groups have a inhibitory effect on melanin production, and thus have completed the present invention. That is, the present invention is as follows.

<1> A melanin production inhibitor (hereinafter, referred to as "the melanin production inhibitor of the present invention"), comprising a compound represented by the following general formula (1) (excluding clotrimazole) and/or a pharmacologically acceptable salt thereof.

[Chem. 1]

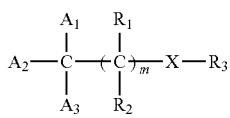

(1)

In the general formula (1), A1, A2, and A3 are each independently selected from a hydrogen atom, an aryl group which may have a substituent, and an aromatic heterocyclic group which may have a substituent, provided that at least one of A1, A2, and A3 is selected from the aryl group and the aromatic heterocyclic group, and a total number of carbon atoms included in A1, A2, and A3 is 6 to 50;

when two or more of A1, A2, and A3 each represent the aryl or the aromatic heterocyclic groups, the adjacent two aryl groups or aromatic heterocyclic groups may be bound to each other via an alkyl chain or an alkenyl chain to further form a ring;

m represents an integer of 0 to 2;

X represents a hetero atom, a hydrogen atom, or a carbon atom;

R1 and R2 are each independently selected from a hydrogen atom and oxo, provided that, when one of R1 and R2 represents the oxo, the other is absent;

R3 is selected from a hydrogen atom, and a hydrocarbon group having 1 to 8 carbon atoms, in which part of hydrogen atoms or carbon atoms may be substituted by a hetero atom, and a number of R3's corresponds to X;

provided that, when two or more R3's are present, the R3's are each independent of each other, and when two or more R3's are present, the adjacent two R3's may be bound to each other to form a ring together with X; and a terminal of R3 may be bound to a carbon atom to which A1, A2, and A3 are bound, thereby forming a ring.

<2> An external preparation for skin for melanin production inhibition (hereinafter, referred to as "the external preparation for skin of the present invention"), comprising the melanin production inhibitor according to Item <1>.

<3> The external preparation for skin according to Item <2>, comprising the melanin production inhibitor in an amount of 0.001 w/w % to 10 w/w % with respect to a total amount of the external preparation for skin.

<4> The external preparation for skin according to Item <2> or <3>, wherein the external preparation for skin is a cosmetic.

<5> Use of a compound represented by the following general formula (1) (excluding clotrimazole) and/or a pharmacologically acceptable salt thereof in manufacture of a melanin production inhibitor.

<6> A method of inhibiting melanin production, administering a compound represented by the following general formula (1) (excluding clotrimazole) and/or a pharmacologically acceptable salt thereof for a subject requiring melanin production inhibition.

Advantageous Effects of Invention

The melanin production inhibitor of the present invention has an excellent inhibitory effect on melanin production. Further, the melanin production inhibitor of the present invention is highly safe, and hence is suitable as a component of an external preparation for skin.

The external preparation for skin of the present invention has an excellent inhibitory effect on melanin production and is highly safe. Therefore, the external preparation for skin of the present invention is suitable as an external preparation for skin which is used for melanin production inhibition, in particular, as a cosmetic.

DESCRIPTION OF EMBODIMENTS

The melanin production inhibitor of the present invention includes a compound represented by the general formula (1) (excluding clotrimazole) and/or a pharmacologically acceptable salt thereof.

The symbols in the general formula (1) are described below.

In the general formula (1), A1, A2, and A3 are each independently selected from a hydrogen atom, an aryl group which may have a substituent, and an aromatic heterocyclic group which may have a substituent. However, at least one of A1, A2, and A3 is selected from the aryl group and the aromatic heterocyclic group, and a total number of carbon atoms included in A1, A2, and A3 is 6 to 50.

The aryl group is preferably selected from phenyl, biphenyl, and naphthyl. The aromatic heterocyclic group is preferably selected from pyridyl and quinolyl.

A1, A2, and A3 are more preferably selected from phenyl and pyridyl.

A preferred combination of A1, A2, and A3 is as follows: all of A1, A2, and A3 each represent phenyl or pyridyl; two of A1, A2, and A3 each represent phenyl or pyridyl, and the other represents a hydrogen atom; one of A1, A2, and A3 represents naphthyl, one of the others represents phenyl or pyridyl, and the other represents a hydrogen atom; and one of A1, A2, and A3 represents quinolyl, one of the others represents phenyl or pyridyl, and the other represents a hydrogen atom.

Further, in the case where the aryl or aromatic heterocyclic group has a substituent, the substituent is preferably selected from fluoro, trifluoromethyl, hydroxyl, amino, a linear or branched alkyl having 1 to 8 carbon atoms, a linear or branched alkyloxy having 1 to 8 carbon atoms, a linear or branched alkylamino having 1 to 8 carbon atoms, a linear or branched dialkylamino having 2 to 8 carbon atoms, a linear or branched acyl having 2 to 9 carbon atoms, and a linear or branched acyloxy having 2 to 9 carbon atoms.

The number of carbon atoms included in the alkyl, alkyloxy, or alkylamino is preferably 1 to 4, more preferably 1 or 2. The number of carbon atoms included in the dialkylamino is preferably 2 to 5, more preferably 2 to 4. The number of carbon atoms included in the acyl or acyloxy is preferably 2 to 5, more preferably 2 or 3.

The substituent is preferably selected from hydroxyl, an alkyl having 1 to 4 carbon atoms, and an alkyloxy having 1 to 4 carbon atoms, more preferably selected from hydroxyl, methyl, and methoxy.

In addition, in the case where the aryl or aromatic heterocyclic group has a substituent, the number of the substituent included in one aryl or aromatic heterocyclic group is preferably 3 or less, more preferably 2 or less.

The total number of carbon atoms included in A1, A2, and A3 is preferably 12 to 36, more preferably 18 to 30.

Further, when two or more of A1, A2, and A3 each represent the aryl or aromatic heterocyclic group, the adjacent two aryl groups or aromatic heterocyclic groups may be bound to each other via an alkyl chain or an alkenyl chain to further form a ring. In this case, the number of carbon atoms included in the alkyl chain or alkenyl chain is preferably 2 to 3.

In the general formula (1), m represents an integer of 0 to 2. m preferably represents 0.

In the general formula (1), the group represented by the following general formula is preferably as follows.

[Chem. 2]

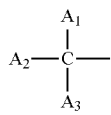

Triphenylmethyl;

[diphenyl(fluorophenyl)]methyl, [bis(fluorophenyl)phenyl]methyl, tris(fluorophenyl)methyl, [diphenyl(trifluoromethylphenyl)]methyl, [bis(trifluoromethylphenyl)phenyl]methyl, tris(trifluoromethylphenyl)methyl;

[diphenyl(hydroxyphenyl)]methyl, [bis(hydroxyphenyl)phenyl]methyl, tris(hydroxyphenyl)methyl;

[diphenyl(methylphenyl)]methyl, [bis(methylphenyl)phenyl]methyl, tris(methylphenyl)methyl, [diphenyl(ethylphenyl)]methyl, [bis(ethylphenyl)phenyl]methyl, tris(ethylphenyl)methyl, [diphenyl(propylphenyl)]methyl, [bis(propylphenyl)phenyl]methyl, tris(propylphenyl)methyl, [diphenyl(butylphenyl)]methyl, [bis(butylphenyl)phenyl]methyl, tris(butylphenyl)methyl;

[diphenyl(methoxyphenyl)]methyl, [bis(methoxyphenyl)phenyl]methyl, tris(methoxyphenyl)methyl, [diphenyl(ethoxyphenyl)]methyl, [bis(ethoxyphenyl)phenyl]methyl, tris(ethoxyphenyl)methyl, [diphenyl(propyloxyphenyl)]methyl, [bis(propyloxyphenyl)phenyl]methyl, tris(propyloxyphenyl)methyl, [diphenyl(butoxyphenyl)]methyl, [bis(butoxyphenyl)phenyl]methyl, tris(butoxyphenyl)methyl;

[bis(aminophenyl)phenyl]methyl, tris(aminophenyl)methyl, [(aminophenyl)diphenyl]methyl;

[diphenyl(N-methylaminophenyl)]methyl, [bis(N-methylaminophenyl)phenyl]methyl, tris(N-methylaminophenyl)methyl, [diphenyl(N-ethylaminophenyl)]methyl, [bis(N-ethylaminophenyl)phenyl]methyl, tris(N-ethylaminophenyl)methyl, [diphenyl(N-propylaminophenyl)]methyl, [bis(N-propylaminophenyl)phenyl]methyl, tris(N-propylaminophenyl)methyl, [diphenyl(N-butylaminophenyl)]methyl, [bis(N-butylaminophenyl)phenyl]methyl, tris(N-butylaminophenyl)methyl;

[diphenyl(N,N-dimethylaminophenyl)]methyl, [bis(N,N-dimethylaminophenyl)phenyl]methyl, tris(N,N-dimethylaminophenyl)methyl, [diphenyl(N,N-diethylaminophenyl)]methyl, [bis(N,N-diethylaminophenyl)phenyl]methyl, tris(N,N-diethylaminophenyl)methyl, [diphenyl(N,N-dipropylaminophenyl)]methyl, [bis(N,N-dipropylaminophenyl)phenyl]methyl, tris(N,N-dipropylaminophenyl)methyl, [diphenyl(N,N-dibutylaminophenyl)]methyl, [bis(N,N-dibutylaminophenyl)phenyl]methyl, tris(N,N-dibutylaminophenyl)methyl;

diphenylmethyl;

[(fluorophenyl)phenyl]methyl, bis(fluorophenyl)methyl, bis(trifluoromethylphenyl)methyl, [(trifluoromethylphenyl)phenyl]methyl;

[(hydroxyphenyl)phenyl]methyl, bis(hydroxyphenyl)methyl;

[(methylphenyl)phenyl]methyl, bis(methylphenyl)methyl, [(ethylphenyl)phenyl]methyl, bis(ethylphenyl)methyl, [(propylphenyl)phenyl]methyl, bis(propylphenyl)methyl, [(butylphenyl)phenyl]methyl, bis(butylphenyl)methyl;

[(methoxyphenyl)phenyl]methyl, bis(methoxyphenyl)methyl, [(ethoxyphenyl)phenyl]methyl, bis(ethoxyphenyl)methyl, [(propyloxyphenyl)phenyl]methyl, bis(propyloxyphenyl)methyl, [(butoxyphenyl)phenyl]methyl, bis(butoxyphenyl)methyl;

[(aminophenyl)phenyl]methyl, bis(aminophenyl)methyl;

[(N-methylaminophenyl)phenyl]methyl, bis(N-methylaminophenyl)methyl, [(N-ethylaminophenyl)phenyl]methyl, bis(N-ethylphenyl)methyl, [(N-propylaminophenyl)phenyl]methyl, bis(N-propylaminophenyl)methyl, [(N-butylaminophenyl)phenyl]methyl, bis(N-butylaminophenyl)methyl,

[(N,N-dimethylaminophenyl)phenyl]methyl, bis(N,N-dimethylaminophenyl)methyl, [(N,N-diethylaminophenyl)phenyl]methyl, bis(N,N-diethylaminophenyl)methyl, [(N,N-dipropylaminophenyl)phenyl]methyl, bis(N,N-dipropylaminophenyl)methyl, [(N,N-dibutylaminophenyl)phenyl]methyl, bis(N,N-dibutylaminophenyl)methyl;

[(naphthyl)phenyl]methyl, bis(naphthyl)methyl, [diphenyl(naphthyl)]methyl, [bis(naphthyl)phenyl]methyl, tris(naphthyl)methyl;

[(biphenyl)phenyl]methyl, bis(biphenyl)methyl, [(biphenyl)diphenyl]methyl, [bis(biphenyl)phenyl]methyl, tris(biphenyl)methyl;

[phenyl(pyridyl)]methyl, bis(pyridyl)methyl, [diphenyl(pyridyl)]methyl, [bis(pyridyl)phenyl]methyl, and tris(pyridyl)methyl.

Of those, there are more preferably given the following groups.

Triphenylmethyl;

[diphenyl(hydroxyphenyl)]methyl, [bis(hydroxyphenyl)phenyl]methyl, tris(hydroxyphenyl)methyl;

[diphenyl(methylphenyl)]methyl, [bis(methylphenyl)phenyl]methyl, tris(methylphenyl)methyl;

[diphenyl(methoxyphenyl)]methyl, [bis(methoxyphenyl)phenyl]methyl, tris(methoxyphenyl)methyl;

diphenylmethyl;

[(hydroxyphenyl)phenyl]methyl, bis(hydroxyphenyl)methyl;

[(methylphenyl)phenyl]methyl, bis(methylphenyl)methyl;

[(methoxyphenyl)phenyl]methyl, bis(methoxyphenyl)methyl;

[(naphthyl)phenyl]methyl;

[(biphenyl)phenyl]methyl;

[diphenyl(pyridyl)]methyl, [bis(pyridyl)phenyl]methyl, and tris(pyridyl)methyl.

In the general formula (1), X represents a hetero atom, a hydrogen atom, or a carbon atom. X preferably represents a hetero atom or a carbon atom. The hetero atom is preferably a nitrogen atom or an oxygen atom.

In the general formula (1), R1 and R2 are each independently selected from a hydrogen atom and oxo. However, when one of R1 and R2 represents the oxo, the other is absent.

In the general formula (1), R3 is selected from a hydrogen atom, or a hydrocarbon group having 1 to 8 carbon atoms, in which part of hydrogen atoms or carbon atoms may be substituted by a hetero atom. Here, in the case where part of carbon atoms in a hydrocarbon group is/are substituted by a hetero atom, the number of carbon atoms included in the hydrocarbon group is defined as a number when it is assumed that such substitution has not been made. The number of R3's corresponds to X. When two or more R3's are present, the R3's are each independently of each other.

The number of carbon atoms included in the hydrocarbon group is preferably 1 to 6.

The hydrocarbon group may be linear, branched chain-like, or cyclic.

Further, the cyclic hydrocarbon group includes a group in which, when two or more R3's are present, the adjacent two R3's are bound to each other to form a ring together with X.

In addition, the terminal of R3 may be bound to a carbon atom to which A1, A2, and A3 are bound, thereby forming a ring.

In the case where the hydrogen atom, or part of hydrogen atoms or carbon atoms is substituted by a hetero atom, the hetero atom is preferably a nitrogen atom or an oxygen atom. The number of the substituted atom is preferably 0 to 4, more preferably 1 to 3.

In the general formula (1), —X—R3 is preferably represented by the following general formula (2).

[Chem. 3]

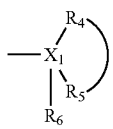

(2)

In the general formula (2), X1 represents a carbon atom or a nitrogen atom. X1 preferably represents a nitrogen atom.

In the general formula (2), R4 and R5 are bound to each other to form, together with X1, a heterocyclic ring or hydrocarbon ring which has 2 to 8 carbon atoms and may have a substituent. Here, the number of the carbon atoms is different from one defined for the number of the carbon atoms included in R3 in the general formula (1), and is defined as an actual number of the carbon atoms.

In the case where the heterocyclic ring or hydrocarbon ring has a substituent, the substituent is preferably selected from an alkyl having 1 to 4 carbon atoms, an alkyloxy having 1 to 4 carbon atoms, hydroxyl, amino, and oxo. Further, in this case, the number of the substituent is preferably 1 to 3, more preferably 1 or 2.

Here, the heterocyclic ring includes any of an aromatic heterocyclic ring, a non-aromatic unsaturated heterocyclic ring, and a saturated heterocyclic ring. The heterocyclic ring is preferably a saturated heterocyclic ring. Further, the number of the carbon atoms included in the heterocyclic ring is preferably 3 to 5, more preferably 4 or 5.

Examples of the aromatic heterocyclic ring include pyrrole, imidazole, and pyrazole.

Preferred examples of the aromatic heterocyclic ring having a substituent include methylpyrrole and methylimidazole.

Examples of the non-aromatic unsaturated heterocyclic ring include pyrroline, imidazoline, and pyrazoline.

Preferred examples of the non-aromatic unsaturated heterocyclic ring having a substituent include methylpyrroline and methylimidazoline.

Examples of the saturated heterocyclic ring include aziridine, azetidine, pyrrolidine, piperidine, azepane (perhydroazepine), azocane (perhydroazocine), piperazine, and morpholine.

Preferred Examples of the saturated heterocyclic ring having a substituent include phthalimide, succinimide, glutarimide, methylpyrrolidine, hydroxypyrrolidine, methylpiperidine, hydroxypiperidine, methylazepane and hydroxyazepane.

Further, the hydrocarbon ring includes any of an aromatic hydrocarbon ring, a non-aromatic unsaturated hydrocarbon ring, and a cycloalkyl ring.

In the general formula (2), R6 represents a hydrogen atom and is present when X1 represents a carbon atom and the heterocyclic ring or hydrocarbon ring is not an aromatic ring. Further, R6 is absent when X1 represents a carbon atom and the heterocyclic ring or hydrocarbon ring is an aromatic ring, and when X1 represents a nitrogen atom.

Further, —X—R3 in the general formula (1) is preferably represented by the following general formula (3).

[Chem. 4]

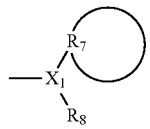

(3)

In the general formula (3), X1 represents a carbon atom or a nitrogen atom. X1 preferably represents a nitrogen atom.

In the general formula (3), R7 represents a hydrocarbon ring group which has 3 to 8 carbon atoms and may have a substituent.

In the case where the hydrocarbon ring has a substituent, the substituent is preferably selected from an alkyl having 1 to 3 carbon atoms, an alkyloxy having 1 to 3 carbon atoms, hydroxyl, amino, and oxo. Further, in this case, the number of the substituent is preferably 1 to 3, more preferably 1 or 2.

Here, the hydrocarbon ring group includes any of an aryl group, a non-aromatic unsaturated hydrocarbon ring group, and a cycloalkyl. The hydrocarbon ring group is preferably a cycloalkyl. Specific examples of the cycloalkyl include cyclopentyl and cyclohexyl.

In the general formula (3), R8 represents a hydrogen atom, and the number of R8's corresponds to X1.

Further, —X—R3 in the general formula (1) is preferably represented by the following general formula (4).

[Chem. 5]

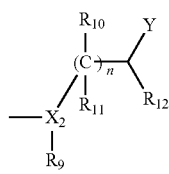

(4)

In the general formula (4), X2 represents a nitrogen atom or an oxygen atom.

n represents an integer of 0 to 5. n preferably represents an integer of 1 to 3.

Y is selected from hydroxyl, amino, and an alkyloxy having 1 to 6 carbon atoms. The alkyloxy is preferably methoxy or ethoxy.

When Y represents amino, X2 preferably represents an oxygen atom.

In the general formula (4), R9 is present when X2 represents a nitrogen atom, and R9 is selected from a hydrogen atom, hydroxyl, and a hydroxyalkyl having 1 to 6 carbon atoms. R9 is preferably selected from a hydrogen atom and a hydroxyalkyl having 1 to 3 carbon atoms. When X2 represents an oxygen atom, R9 is absent.

In the general formula (4), R10, R11, and R12 are each independently selected from a hydrogen atom, hydroxyl, oxo, and a hydroxyalkyl having 1 to 5 carbon atoms. However, when one of R10 and R11 represents oxo, the other is absent. R10, R11, and R12 are preferably selected from a hydrogen atom, oxo, and a hydroxyalkyl having 1 to 3 carbon atoms, more preferably selected from a hydrogen atom and a hydroxyalkyl having 1 to 3 carbon atoms.

The group represented by the general formula (4) preferably includes the following ones.

2-Hydroxyethyloxy, 3-hydroxypropyloxy, 2-aminoethyloxy, 3-aminopropyloxy, ethylamino, 2-hydroxyethylamino, 3-hydroxypropylamino, 2-aminoethylamino, bis(2-hydroxyethyl)amino, 2,3-dihydroxypropyloxy, carboxymethyl, carboxy(hydroxymethyl)methyl, ethoxycarbonylmethylamino, and methoxycarbonyl(hydroxymethyl)amino.

The compound represented by the general formula (1) of the present invention is preferably represented by the following general formula (5).

[Chem. 6]

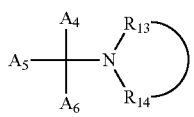

(5)

In the general formula (5), A4, A5, and A6 are each independently selected from phenyl and pyridyl which may be substituted by methyl, methoxy, or hydroxyl.

R13 and R14 are bound to each other to form, together with a nitrogen atom represented by N, a saturated heterocyclic ring which has 4 or 5 carbon atoms and may be substituted by hydroxyl or oxo.

Preferred examples of the saturated heterocyclic ring include pyrrolidine, piperidine, piperazine, morpholine, succinimide, and pyrrolidinol. More preferred examples thereof include pyrrolidine, piperidine, piperazine, and morpholine.

The compound represented by the general formula (5) specifically includes the following compounds.

1-(Triphenylmethyl)pyrrolidine, 1-[[diphenyl(methylphenyl)]methyl]pyrrolidine, 1-[[bis(methylphenyl)phenyl]methyl]pyrrolidine, 1-[tris(methylphenyl)methyl]pyrrolidine, 1-[[diphenyl(methoxyphenyl)]methyl]pyrrolidine, 1-[[bis(methoxyphenyl)phenyl]methyl]pyrrolidine, 1-[tris(methoxyphenyl)methyl]pyrrolidine, 1-[[diphenyl(hydroxyphenyl)methyl]pyrrolidine, 1-[[bis(hydroxyphenyl)phenyl]methyl]pyrrolidine, 1-[tris(hydroxyphenyl)methyl]pyrrolidine;

1-(triphenylmethyl)piperidine, 1-[[diphenyl(methylphenyl)]methyl]piperidine, 1-[[bis(methylphenyl)phenyl]methyl]piperidine, 1-[tris(methylphenyl)methyl]piperidine, 1-[[diphenyl(methoxyphenyl)]methyl]piperidine, 1-[[bis(methoxyphenyl)phenyl]methyl]piperidine, 1-[tris(methoxyphenyl)methyl]piperidine, 1-[[diphenyl(hydroxyphenyl)]methyl]piperidine, 1-[[bis(hydroxyphenyl)phenyl]methyl]piperidine, 1-[tris(hydroxyphenyl)methyl]piperidine;

1-(triphenylmethyl)piperazine, 1-[[diphenyl(methylphenyl)]methyl]piperazine, 1-[[bis(methylphenyl)phenyl]methyl]piperazine, 1-[tris(methylphenyl)methyl]piperazine, 1-[[diphenyl(methoxyphenyl)]methyl]piperazine, 1-[[bis(methoxyphenyl)phenyl]methyl]piperazine, 1-[tris(methoxyphenyl)methyl]piperazine, 1-[[diphenyl(hydroxyphenyl)]methyl]piperazine, 1-[[bis(hydroxyphenyl)phenyl]methyl]piperazine, 1-[tris(hydroxyphenyl)methyl]piperazine;

1-(triphenylmethyl)morpholine, 1-[[diphenyl(methylphenyl)]methyl]morpholine, 1-[[bis(methylphenyl)phenyl]methyl]morpholine, 1-[tris(methylphenyl)methyl]morpholine, 1-[[diphenyl(methoxyphenyl)]methyl]morpholine, 1-[[bis(methoxyphenyl)phenyl]methyl]morpholine, 1-[tris(methoxyphenyl)methyl]morpholine, 1-[[diphenyl(hydroxyphenyl)]methyl]morpholine, 1-[[bis(hydroxyphenyl)phenyl]methyl]morpholine, and 1-[tris(hydroxyphenyl)methyl]morpholine.

Of those, Compounds 5 and 6 described below are particularly preferred.

[Chem. 7]

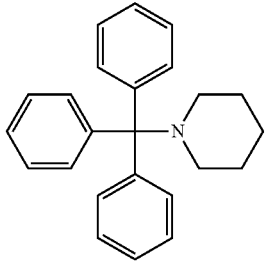

(Compound 5)

1-(Triphenylmethyl)piperidine

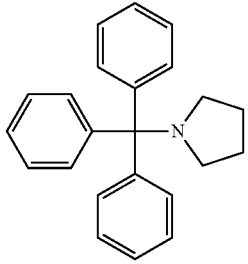

(Compound 6)

1-(Triphenylmethyl)pyrrolidine

Further, the compound represented by the general formula (1) of the present invention is preferably represented by the following general formula (6).

[Chem. 8]

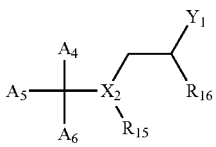

(6)

In the general formula (6), A4, A5, and A6 are each independently selected from phenyl and pyridyl, each of which may be substituted by methyl, methoxy, or hydroxyl.

X2 represents a nitrogen atom or an oxygen atom.

In the general formula (6), Y1 represents hydroxyl or amino.

When Y1 represents amino, X2 preferably represents an oxygen atom.

In the general formula (6), R15 is present when X2 represents a nitrogen atom, and R15 is selected from a hydrogen atom, hydroxyl, and a hydroxyalkyl having 1 to 3 carbon atoms. In this case, R15 is preferably selected from a hydrogen atom and a hydroxyalkyl having 1 to 3 carbon atoms. When X2 represents an oxygen atom, R15 is absent.

In the general formula (6), R16 is selected from a hydrogen atom, hydroxyl, and a hydroxyalkyl having 1 to 3 carbon atoms. R16 is preferably selected from a hydrogen atom and a hydroxyalkyl having 1 to 3 carbon atoms.

The compound represented by the general formula (6) specifically includes the following compounds.

2-(Triphenylmethyloxy)ethanol, 2-[[diphenyl(methylphenyl)]methyloxy]ethanol, 2-[[bis(methylphenyl)phenyl]methyloxy]ethanol, 2-[tris(methylphenyl)methyloxy]ethanol, 2-[[diphenyl(methoxyphenyl)]methyloxy]ethanol, 2-[[bis(methoxyphenyl)phenyl]methyloxy]ethanol, 2-[tris(methoxyphenyl)methyloxy]ethanol;

2-[[diphenyl(hydroxyphenyl)]methyloxy]ethanol, 2-[[bis(hydroxyphenyl)phenyl]methyloxy]ethanol, 2-[tris(hydroxyphenyl)methyloxy]ethanol, 2-[[diphenyl(fluorophenyl)]methyloxy]ethanol, 2-[[bis(fluorophenyl)phenyl]methyloxy]ethanol, 2-[tris(fluorophenyl)methyloxy]ethanol;

3-(triphenylmethyloxy)propanol, 3-[[diphenyl(methylphenyl)]methyloxy]propanol, 3-[[bis(methylphenyl)phenyl]methyloxy]propanol, 3-[tris(methylphenyl)methyloxy]propanol, 3-[[diphenyl(methoxyphenyl)]methyloxy]propanol, 3-[[bis(methoxyphenyl)phenyl]methyloxy]propanol, 3-[tris(methoxyphenyl)methyloxy]propanol, 3-[[diphenyl(hydroxyphenyl)]methyloxy]propanol, 3-[[bis(hydroxyphenyl)phenyl]methyloxy]propanol, 3-[tris(hydroxyphenyl)methyloxy]propanol, 3-[[diphenyl(fluorophenyl)]methyloxy]propanol, 3-[[bis(fluorophenyl)phenyl]methyloxy]propanol, 3-[tris(fluorophenyl)methyloxy]propanol;

2-(triphenylmethyloxy)ethylamine, 2-[[diphenyl(methylphenyl)]methyloxy]ethylamine, 2-[[bis(methylphenyl)phenyl]methyloxy]ethylamine, 2-[tris(methylphenyl)methyloxy]ethylamine, 2-[[diphenyl(methoxyphenyl)]methyloxy]ethylamine, 2-[[bis(methoxyphenyl)phenyl]methyloxy]ethylamine, 2-[tris(methoxyphenyl)methyloxy]ethylamine, 2-[[diphenyl(fluorophenyl)]methyloxy]ethylamine, 2-[[bis(fluorophenyl)phenyl]methyloxy]ethylamine, 2-[tris(fluorophenyl)methyloxy]ethylamine;

3-(triphenylmethyloxy)propylamine, 3-[[diphenyl(methylphenyl)]methyloxy]propylamine, 3-[[bis(methylphenyl)phenyl]methyloxy]propylamine, 3-[tris(methylphenyl)methyloxy]propylamine, 3-[[diphenyl(methoxyphenyl)]methyloxy]propylamine, 3-[[bis(methoxyphenyl)phenyl]methyloxy]propylamine, 3-[tris(methoxyphenyl)methyloxy]propylamine, 3-[[diphenyl(fluorophenyl)]methyloxy]propylamine, 3-[[bis(fluorophenyl)phenyl]methyloxy]propylamine, 3-[tris(fluorophenyl)methyloxy]propylamine;

2-(triphenylmethylamino)ethanol, 2-[[diphenyl(methylphenyl)]methylamino]ethanol, 2-[[bis(methylphenyl)phenyl]methylamino]ethanol, 2-[tris(methylphenyl)methylamino]ethanol, 2-[[diphenyl(methoxyphenyl)]methylamino]ethanol, 2-[[bis(methoxyphenyl)phenyl]methylamino]ethanol, 2-[tris(methoxyphenyl)methylamino]ethanol, 2-[[diphenyl(fluorophenyl)]methylamino]ethanol, 2-[[bis(fluorophenyl)phenyl]methylamino]ethanol, 2-[tris(fluorophenyl)methylamino]ethanol;

3-(triphenylmethylamino)propanol, 3-[[diphenyl(methylphenyl)]methylamino]propanol, 3-[[bis(methylphenyl)phenyl]methylamino]propanol, 3-[tris(methylphenyl)methylamino]propanol, 3-[[diphenyl(methoxyphenyl)]methylamino]propanol, 3-[[bis(methoxyphenyl)phenyl]methylamino]propanol, 3-[tris(methoxyphenyl)methylamino]propanol, 3-[[diphenyl(fluorophenyl)]methylamino]propanol, 3-[[bis(fluorophenyl)phenyl]methylamino]propanol, 3-[tris(fluorophenyl)methylamino]propanol;

N-triphenylmethyl-N-ethylamine, N-[[diphenyl(methylphenyl)]methyl]-N-ethylamine, N-[[bis(methylphenyl)phenyl]methyl]-N-ethylamine, N-[tris(methylphenyl)methyl]-N-ethylamine, N-[[diphenyl(methoxyphenyl)]methyl]-N-ethylamine, N-[[bis(methoxyphenyl)phenyl]methyl]-N-ethylamine, and N-[tris(methoxyphenyl)methyl]-N-ethylamine.

Of those, Compounds 2 to 4 described below are particularly preferred.

[Chem. 9]

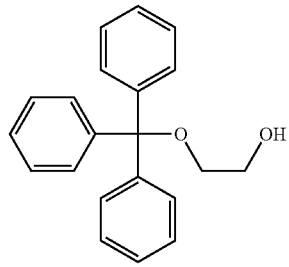

(Compound 2)

2-(Triphenylmethyloxy)ethanol

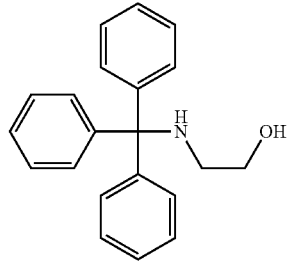

(Compound 3)

2-(Triphenylmethylamino)ethanol

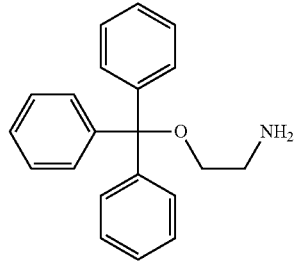

(Compound 4)

2-(Triphenylmethyloxy)ethylamine

Further, —X—R3 in the general formula (1) is preferably represented by the following general formula (7).

[Chem. 10]

$$-X_3-H_p \qquad (7)$$

In the general formula (7), X3 represents a hetero atom, a hydrogen atom, or a carbon atom.

In the general formula (7), the number of p's corresponds to X3.

The group represented by the general formula (7) are preferably selected from an amino group, a hydroxyl group, and a methyl group.

Of compounds each represented by the general formula (1) in which —X—R3 is represented by the general formula (7), the following compounds are particularly preferred.

[Chem. 11]

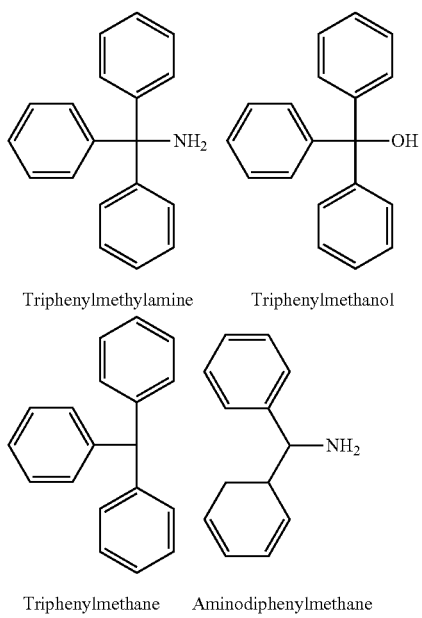

Triphenylmethylamine   Triphenylmethanol

Triphenylmethane   Aminodiphenylmethane

The compound represented by the general formula (1) preferably is free of imidazole skeleton. Because of the structure free of an imidazole skeleton, the compound does not exhibit an antimycotic activity and serves as a melanin production inhibitor which is highly safe.

The compound represented by the general formula (1) preferably has a minimum inhibitory concentration ($MIC_{80}$), which is the minimum concentration needed to inhibit the growth of dermatophytes by 80% or more and is measured by the method described in Test Example 5 later, of larger than that of clotrimazole. The compound represented by the general formula (1) preferably has $MIC_{80}$ 10 times or more, more preferably 20 times or more, still more preferably 50 times or more, particularly preferably 100 times or more that of clotrimazole.

This is considered from the view point of safety in the case of using the compound for an external preparation for skin as a melanin production inhibitor.

Further, the compound represented by the general formula (1) is preferably free of an effect of inhibiting the expression of tyrosinase protein at a minimum effective dose for melanin production inhibition.

It can be confirmed whether or not the compound has the effect of inhibiting the expression of tyrosinase protein at the minimum effective dose for melanin production inhibition by, for example, measuring a tyrosinase activity at a minimum concentration, in the case where the amount of melanin production measured by the method described in Test Example 1 later is 40% or less compared with the control, by the method described in Test Example 7 later. Here, in the case where the tyrosinase activity is 80% or more (as) compared with the control, preferably 90% or more (as) compared with the control, more preferably is the same as that of the control, the compound can be evaluated to have no effect of inhibiting the expression of tyrosinase protein. It should be noted that the phrase "the same as that of the control" refers to the case where the tyrosinase activity is 95 to 100% (as) compared with the control.

The compound represented by the general formula (1), for example, can be produced by a conventional method using a commercially available raw material in accordance with a method described in J. Org. Chem., 66 (23), 7615-7625 (2001). Specific production examples are described later.

The compound represented by the general formula (1) is converted into the form of a salt by treatment with a pharmacologically acceptable acid or base, and the salt may be used as a melanin production inhibitor. Suitable examples of the salts include: mineral acid salts such as a hydrochloride, a sulfate, a nitrate, a phosphate, and a carbonate; organic acid salts such as a maleate, a fumarate, an oxalate, a citrate, a lactate, a tartrate, a methanesulfonate, a paratoluenesulfonate, and a benzenesulfonate; alkali metal salts such as a sodium salt and a potassium salt; alkali earth metal salts such as a calcium salt and a magnesium salt; organic amine salts such as a triethylamine salt, a triethanolamine salt, an ammonium salt, a monoethanolamine salt, and a piperidine salt; and basic amino acid salts such as a lysine salt and an alginate.

The inhibitory effect on melanin production of the melanin production inhibitor of the present invention can be measured using thiouracil which is incorporated specifically into cells in a melanin synthesis process in the cells. For example, the amount of melanin production can be measured by measuring an amount of thiouracil incorporated into cells by measuring an amount of radiation with radiolabeled thiouracil. In this case, as the amount of radiation becomes smaller, the amount of melanin production becomes smaller, and hence the inhibitor can be evaluated to have a large inhibitory effect on melanin production.

The external preparation for skin of the present invention includes the above-mentioned melanin production inhibitor of the present invention. The external preparation for skin of the present invention may include only one kind of the melanin production inhibitor of the present invention or may include two or more kinds of the inhibitors.

The content of the melanin production inhibitor of the present invention in the external preparation for skin is preferably 0.001 to 10 w/w %, more preferably 0.01 to 5 w/w %, still more preferably 0.1 to 3 w/w % with respect to the total amount of the external preparation for skin.

The external preparation for skin of the present invention is used for the inhibition of melanin production. Applications "for the inhibition of melanin production" include applications for objectives mainly intended to be achieved by the inhibition of melanin production, such as applications "for ameliorating pigmentation", "for whitening", and "for ameliorating age spots".

The compound represented by the general formula (1) and/or a pharmacologically acceptable salt thereof have/has a wide absorbance peak with a high absorption coefficient in the ultraviolet region. Therefore, the external preparation for skin of the present invention is effective for protection against ultraviolet rays. That is, the external preparation for skin of the present invention exerts not only the inhibitory effect on melanin production but also an ultraviolet absorption effect, and hence the preparation has the following two effects: prevention of tanning, i.e., an effect of preventing darkening of undarkened skin and preventing further darkening of skin which has begun to darken; and amelioration of tanning, i.e., an effect of ameliorating already darkened skin compared with normal skin color into a normal color, and ameliorating an originally dark skin color into a desirable white skin color.

Further, the external preparation for skin of the present invention is preferably a cosmetic.

Here, the term "cosmetic" includes not only cosmetics specified by the pharmaceutical affairs law of each country but also cosmetics classified on the border with external drug for skin, such as quasi-drugs in Japan and drug-including cosmetics in Taiwan.

The external preparation for skin of the present invention can include optional ingredients used commonly in an external preparation for skin in addition to the melanin production inhibitor of the present invention. Preferred examples of such optional ingredients include: oils/waxes such as macadamia nut oil, avocado oil, corn oil, olive oil, rapeseed oil, sesame oil, castor oil, safflower oil, cottonseed oil, jojoba oil, coconut oil, palm oil, liquid lanolin, cured coconut oil, cured oil, Japan wax, cured castor oil, beeswax, candelilla wax, carnauba wax, ibota wax, lanolin, reduced lanolin, hard lanolin, and jojoba wax; hydrocarbons such as liquid paraffin, squalane, pristane, ozokerite, paraffin, ceresin, vaseline, and microcrystalline wax; higher fatty acids such as oleic acid, isostearic acid, lauric acid, myristic acid, palmitic acid, stearic acid, behenic acid, and undecylenic acid; higher alcohols such as cetyl alcohol, stearyl alcohol, isostearyl alcohol, behenyl alcohol, octyldodecanol, myristyl alcohol, and cetostearyl alcohol; synthetic ester oils such as cetyl isooctanoate, isopropyl myristate, hexyldecyl isostearate, diisopropyl adipate, di-2-ethylhexyl sebacate, cetyl lactate, diisostearyl malate, ethylene glycol di-2-ethyl hexanoate, neopentylglycol dicaprate, glyceryl di-2-heptylundecanoate, glyceryl tri-2-ethylhexanoate, trimethylolpropane tri-2-ethylhexanoate, trimethylolpropane triisostearate, and pentane erythrite tetra-2-ethylhexanoate; chain polysiloxanes such as dimethylpolysiloxane, methylphenylpolysiloxane, and diphenylpolysiloxane; cyclic polysiloxanes such as octamethylcyclotetrasiloxane, decamethylcyclopentasiloxane, and dodecamethylcyclohexanesiloxane; oil agents such as silicone oil including modified polysiloxanes such as amino-modified polysiloxane, polyether-modified polysiloxane, alkyl-modified polysiloxane, and fluorine-modified polysiloxane; anionic surfactants such as fatty acid soaps (such as sodium laurate and sodium palmitate), potassium laurylsulfate, and triethanolamine alkylsulfate ether; cationic surfactants such as trimethyl ammonium stearyl chloride, benzalkonium chloride, and laurylamine oxide; amphoteric surfactants such as imidazoline-based amphoteric surfactants (such as a 2-cocoyl-2-imidazolinium hydroxide-1-carboxyethyloxy disodium salt), betaine-based surfactants (such as alkyl betaine, amide betaine, and sulfo betaine), and acylmethyl taurine; nonionic surfactants such as sorbitan fatty acid esters (such as sorbitan monostearate and sorbitan sesquioleate), glycerin fatty acid esters (such as glycerin monostearate), propyleneglycol fatty acid esters (such as propyleneglycol monostearate), cured castor oil derivatives, glycerol alkyl ether, POE sorbitan fatty acid esters (such as POE sorbitan monooleate and polyoxyethylene sorbitan monostearate), POE sorbitol fatty acid esters (such as POE-sorbitol monolaurate), POE glycerol fatty acid esters (such as POE-glycerin monoisostearate), POE fatty acid esters (such as polyethyleneglycol monooleate and POE distearate), POE alkyl ethers (such as POE2-octyldodecyl ether), POE alkylphenyl ethers (such as POE nonylphenyl ether), pluronic types, POE/POP alkyl ethers (such as POE/POP2-decyltetradecyl ether), tetronic types, POE castor oil/cured castor oil derivatives (such as POE castor oil and POE cured castor oil), sucrose fatty acid ester, and alkyl glucoside; polyvalent alcohols such as polyethylene glycol, glycerin, 1,3-butylene glycol, erythritol, sorbitol, xylitol, maltitol, propylene glycol, dipropylene glycol, diglycerin, isoprene glycol, 1,2-pentanediol, 2,4-hexanediol, 1,2-hexanediol, and 1,2-octanediol; moisture-retaining ingredients such as sodium pyrrolidone carboxylate, lactate, and sodium lactate; fine particles such as mica, talc, kaolin, synthetic mica, calcium carbonate, magnesium carbonate, silicic anhydride (silica), aluminum oxide, and barium sulfate, whose surfaces may be treated; inorganic pigments such as red iron oxide, yellow iron oxide, black iron oxide, cobalt oxide, ultramarine blue, iron blue, titanium oxide, and zinc oxide, whose surfaces may be treated; pearl agents such as mica titanium, fish scale foil, and bismuth oxychloride, whose surfaces may be treated; organic dyes such as Red No. 202, Red No. 228, Red No. 226, Yellow No. 4, Blue No. 404, Yellow No. 5, Red No. 505, Red No. 230, Red No. 223, Orange No. 201, Red No. 213, Yellow No. 204, Yellow No. 203, Blue No. 1, Green No. 201, Purple No. 201, and Red No. 204, which may be laked; organic fine particles such as polyethylene powder, polymethyl methacrylate, nylon powder, and organopolysiloxane elastomer; p-aminobenzoate-based ultraviolet absorbent; an anthranilate-based ultraviolet absorbent; a salicylate-based ultraviolet absorbent; a cinnamate-based ultraviolet absorbent; a benzophenone-based ultraviolet absorbent; a sugar-based ultraviolet absorbent; ultraviolet absorbents such as 2-(2'-hydroxy-5'-t-octylphenyl)benzotriazole and 4-methoxy-4'-t-butyldibenzoylmethane; lower alcohols such as ethanol and isopropanol; vitamins such as vitamin A or derivatives thereof; vitamin B types such as vitamin $B_6$ hydrochloride, vitamin $B_6$ tripalmitate, vitamin $B_6$ dioctanoate, vitamin $B_2$ or derivatives thereof, vitamin $B_{12}$, and vitamin $B_{15}$ or derivatives thereof; vitamin E types such as α-tocopherol, β-tocopherol, γ-tocopherol, and vitamin E acetate; vitamin D types; vitamin H; pantothenic acid; pantethine; and pyrroloquinoline quinone; and antibacterial agents such as phenoxyethanol.

The external preparation for skin of the present invention can be produced by treating the melanin production inhibitor of the present invention and the optional ingredient as mentioned above in accordance with a conventional method and processing the resultant product into various preparations such as a lotion, a milky liquid, an essence, a cream, and a pack.

PRODUCTION EXAMPLES OF COMPOUNDS

Production examples of the compounds each represented by the general formula (1) are shown below.

Production Example 1

Synthesis of 1-(triphenylmethyl)imidazole (Compound 1)

[Chem. 12]

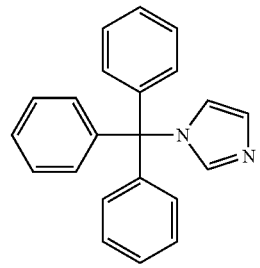

(Compound 1)

Compound 1 was synthesized by a method described in JP 53-16879 A. It should be noted that Compound 1 may be purchased as a reagent from Wako Pure Chemical Industries, Ltd.

Production Example 2

Synthesis of 2-(triphenylmethyloxy)ethanol (Compound 2)

[Chem. 13]

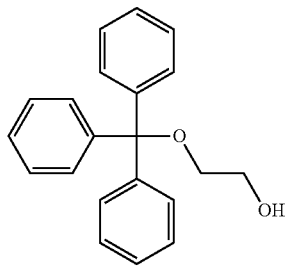

(Compound 2)

Ethylene glycol (3.10 g, 49.9 mmol) (Wako Pure Chemical Industries, Ltd.) and triphenylchloromethane (1.39 g, 49.9 mmol) (Wako Pure Chemical Industries, Ltd.) were dissolved in pyridine (6 mL) (Wako Pure Chemical Industries, Ltd.), and the solution was heated to 45° C. and stirred for 2 hours. Water (50 mL) was poured into the reaction solution, and mixture was extracted with toluene (Wako Pure Chemical Industries, Ltd.). The organic layer was dried with an hydrous sodium sulfate (Wako Pure Chemical Industries, Ltd.), and the solvent was distilled of funder reduced pressure. The residue was subjected to silica gel column chromatography (chloroform (Wako Pure Chemical Industries, Ltd.):methanol (Wako Pure Chemical Industries, Ltd.)=9:1), to thereby obtain the title compound (0.37 g, 24% yield).

m.p. 103-106° C.

$^1$H-NMR (CDCl$_3$): δ3.26 (t, J=4.5 Hz, 2H), 3.75 (t, J=4.5 Hz, 2H), 7.23-7.54 (m, 15H).

IR (cm$^{-1}$): 3337, 1448, 1093, 1061.

Production Example 3

Synthesis of 2-(triphenylmethylamino)ethanol (Compound 3)

[Chem. 14]

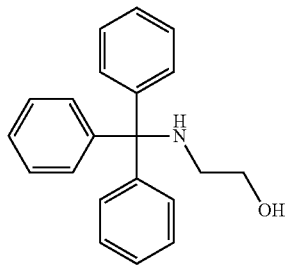

(Compound 3)

Triphenylchloromethane (1.00 g, 3.58 mmol) (Wako Pure Chemical Industries, Ltd.) and aminoethanol (2.00 g, 32.7 mmol) were dissolved in acetonitrile (5 mL), and the solution was stirred at room temperature overnight. Water (100 mL) was poured into the reaction solution, and the precipitates were suction-filtered and then dried. The solid product was recrystallized from a mixed solvent of ethanol (Wako Pure Chemical Industries, Ltd.) and water, to thereby obtain the title compound (0.43 g, 39% yield).

m.p. 94-97° C.

$^1$H-NMR (DMSO): δ2.07 (t, J=6.0 Hz, 2H), 3.51 (t, J=6.0 Hz, 2H), 7.15-7.42 (m, 15H).

IR (cm$^{-1}$): 3244, 1488, 1442, 1025.

Production Example 4

Synthesis of 2-(triphenylmethyloxy)ethylamine (Compound 4)

[Chem. 15]

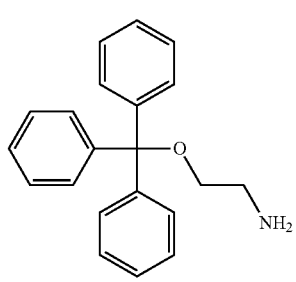

(Compound 4)

Triphenylchloromethane (1.00 g, 3.58 mmol) (Wako Pure Chemical Industries, Ltd.) and ethanolamine hydrochloride (1.00 g, 10.3 mmol) (Wako Pure Chemical Industries, Ltd.) were dissolved in pyridine (4 mL), and the solution was stirred at room temperature for 3 days. Water (200 mL) was poured into the reaction solution, and the precipitates were suction-filtered. The solid matters were suspended in diethyl ether, and 3 (N) hydrochloric acid (Wako Pure Chemical Industries, Ltd.) was added thereto, followed by stirring at room temperature for 15 minutes. The insoluble matters were suction-filtered. The insoluble matters were dissolved in a mixed solution of ethyl acetate (Wako Pure Chemical Industries, Ltd.) and a saturated aqueous solution of sodium hydrogen carbonate (Wako Pure Chemical Industries, Ltd.), and the mixture was shaken, followed by the separation of the organic layer. The organic layer was dried with anhydrous sodium sulfate (Wako Pure Chemical Industries, Ltd.), and then suction-filtered and concentrated under reduced pressure, to thereby obtain the title compound (0.31 g, 28% yield).

m.p. 87-89° C.

$^1$H-NMR (CDCl$_3$): δ2.88 (t, J=5.1 Hz, 2H), 3.14 (t, J=5.1 Hz, 2H) 7.24-7.51 (m, 15H).

IR (cm$^{-1}$): 3378, 1594, 1448, 1054.

Production Example 5

Synthesis of 1-(triphenylmethyl)piperidine (Compound 5)

[Chem. 16]

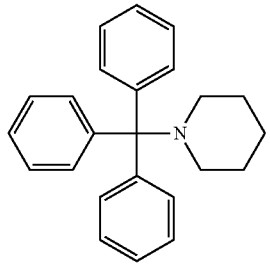

(Compound 5)

Piperidine (1.50 g, 17.6 mmol) (Wako Pure Chemical Industries, Ltd.), triphenylchloromethane (5.40 g, 19.4 mmol) (Wako Pure Chemical Industries, Ltd.), and potassium carbonate (2.68 g, 19.4 mmol) (Wako Pure Chemical Industries, Ltd.) were added to acetonitrile (30 mL) (Wako Pure Chemical Industries, Ltd.), and the mixture was refluxed for 5 hours. A saturated aqueous solution of sodium hydrogen carbonate (Wako Pure Chemical Industries, Ltd.) was added to the reaction solution, and mixture was extracted with ethyl acetate (Wako Pure Chemical Industries, Ltd.). The organic layer was dried with anhydrous sodium sulfate (Wako Pure Chemical Industries, Ltd.), and the solvent was distilled off under reduced pressure. The residue was recrystallized from a mixed solvent of chloroform (Wako Pure Chemical Industries, Ltd.) and n-hexane (Wako Pure Chemical Industries, Ltd.), to thereby obtain the title compound (1.80 g, 31% yield).

m.p. 156-158° C.

$^1$H-NMR (CDCl$_3$): δ0.70-3.50 (m, 10H), 7.14-7.80 (m, 15H).

IR (cm$^{-1}$): 2923, 1485, 1448, 708.

Production Example 6

Synthesis of 1-(triphenylmethyl)pyrrolidine (Compound 6)

[Chem. 17]

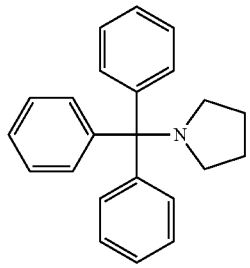

(Compound 6)

Pyrrolidine (0.26 g, 3.66 mmol) (Wako Pure Chemical Industries, Ltd.), triphenylchloromethane (1.02 g, 3.66 mmol) (Wako Pure Chemical Industries, Ltd.), and potassium carbonate (0.51 g, 3.66 mmol) (Wako Pure Chemical Industries, Ltd.) were added to acetonitrile (30 mL) (Wako Pure Chemical Industries, Ltd.), and the mixture was refluxed for 5 hours. A saturated aqueous solution of sodium hydrogen carbonate (Wako Pure Chemical Industries, Ltd.) was added to the reaction solution, and mixture was extracted with ethyl acetate (Wako Pure Chemical Industries, Ltd.). The organic layer was dried with anhydrous sodium sulfate (Wako Pure Chemical Industries, Ltd.), and the solvent was distilled off under reduced pressure. The residue was subjected to silica gel column chromatography (n-hexane (Wako Pure Chemical Industries, Ltd.):ethyl acetate (Wako Pure Chemical Industries, Ltd.)=9:1 as an eluent)), to thereby obtain the title compound (0.45 g, 80% yield).

m.p. 127-129° C.

$^1$H-NMR (CDCl$_3$): δ1.53-1.65 (m, 4H), 2.00-2.30 (4H, m), 7.11-7.28 (m, 5H), 7.48-7.52 (m, 10H).

IR (cm$^{-1}$): 2961, 2819, 1486, 1448, 711.

Production Example 7

Synthesis of 1-(triphenylmethyl)piperazine (Compound 7)

[Chem. 18]

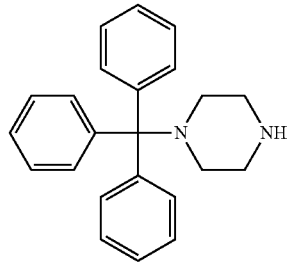

(Compound 7)

Piperazine (1.00 g, 11.6 mmol) (Wako Pure Chemical Industries, Ltd.) was dissolved in N,N-dimethylformamide (25 mL) (Wako Pure Chemical Industries, Ltd.), and triphenylchloromethane (0.65 g, 2.33 mmol) (Wako Pure Chemical Industries, Ltd.) was added little by little, and the mixture was stirred at room temperature overnight. Water was poured into the reaction solution, and mixture was extracted with ethyl acetate (Wako Pure Chemical Industries, Ltd.). The organic layer was dried with anhydrous sodium sulfate (Wako Pure Chemical Industries, Ltd.), and the solvent was distilled off under reduced pressure. The residue was subjected to silica gel column chromatography (chloroform (Wako Pure Chemical Industries, Ltd.):methanol (Wako Pure Chemical Industries, Ltd.)=9:1 as an eluent). The residue was dissolved in ethyl acetate and a saturated aqueous solution of sodium hydrogen carbonate (Wako Pure Chemical Industries, Ltd.), and the mixture was shaken, followed by separation of the organic layer. The organic layer was dried with anhydrous sodium sulfate (Wako Pure Chemical Industries, Ltd.), and then the solvent was distilled off under reduced pressure, to thereby obtain the title compound (0.76 g, 99% yield).

$^1$H-NMR (CDCl$_3$): δ 1.20-1.92 (m, 4H), 2.68-3.20 (m, 4H), 7.12-7.29 (10H, m), 7.32-7.60 (m, 5H)

Production Example 8

Synthesis of N-(triphenylmethyl)morpholine (Compound 8)

[Chem. 19]

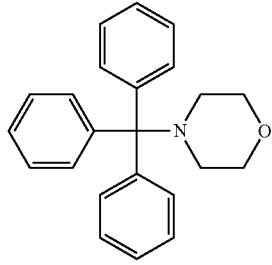

(Compound 8)

Morpholine (0.47 g, 5.39 mmol) (Wako Pure Chemical Industries, Ltd.), triphenylchloromethane (1.50 g, 5.39 mmol) (Wako Pure Chemical Industries, Ltd.), and potassium carbonate (0.75 g, 5.39 mmol) (Wako Pure Chemical Industries, Ltd.) were added to N,N-dimethylformamide (5 mL) (Wako Pure Chemical Industries, Ltd.), and the mixture was stirred at room temperature overnight. A saturated aqueous solution of sodium hydrogen carbonate (Wako Pure Chemical Industries, Ltd.) was added to the reaction solution, and mixture was extracted with ethyl acetate (Wako Pure Chemical Industries, Ltd.). The organic layer was dried with anhydrous sodium sulfate, and the solvent was distilled off under reduced pressure. The residue was subjected to silica gel column chromatography (n-hexane (Wako Pure Chemical Industries, Ltd.):ethyl acetate (Wako Pure Chemical Industries, Ltd.)=9:1 as an eluent), to thereby obtain the title compound (0.42 g, 71% yield).

m.p. 168-172° C.
$^1$H-NMR (CDCl$_3$): δ1.45-1.65 (m, 4H), 3.82-3.83 (m, 4H), 7.13-7.29 (m, 10H), 7.47-7.50 (m, 5H).
IR (cm$^{-1}$): 2846, 1490, 1447, 709.

Production Example 9

Synthesis of [diphenyl(4-pyridyl)]methanol (Compound 9)

[Chem. 20]

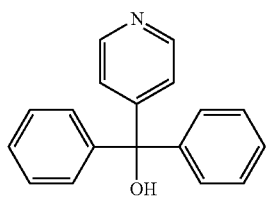

(Compound 9)

A Grignard reagent was prepared from magnesium (0.21 g, 8.64 mmol) (Wako Pure Chemical Industries, Ltd.) and bromobenzene (1.35 g, 8.60 mmol) (Wako Pure Chemical Industries, Ltd.). 4-Benzoylpyridine (0.52 g, 28.4 mmol) (Wako Pure Chemical Industries, Ltd.) was dissolved in tetrahydrofuran (10 mL) (Wako Pure Chemical Industries, Ltd.), and the Grignard reagent was added dropwise, followed by stirring at room temperature for 5 hours. A saturated aqueous solution of ammonium chloride (Wako Pure Chemical Industries, Ltd.) was added to the reaction solution, and mixture was extracted with ethyl acetate (Wako Pure Chemical Industries, Ltd.). The organic layer was dried with anhydrous sodium sulfate (Wako Pure Chemical Industries, Ltd.), and the solvent was distilled off under reduced pressure. The residue was subjected to silica gel column chromatography (chloroform (Wako Pure Chemical Industries, Ltd.) as an eluent), to thereby obtain the title compound (0.72 g, 97% yield).

$^1$H-NMR (CDCl$_3$): δ2.98 (m, 1H), 7.23-7.35 (m, 12H), 8.53-8.55 (m, 2H).

Production Example 10

Synthesis of 1-{[diphenyl(4-pyridyl)]methyl}piperidine (Compound 10)

[Chem. 21]

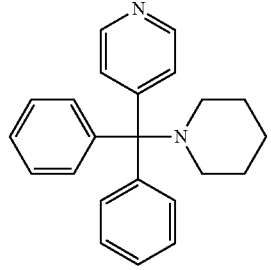

(Compound 10)

Thionyl chloride (1 mL) (Wako Pure Chemical Industries, Ltd.) was added to Compound 9 described above (0.30 g, 1.15 mmol), and the mixture was refluxed for 30 minutes. Then, the solvent was distilled off under reduced pressure. The residue was dissolved in acetonitrile (20 mL), and piperidine (0.75 g, 8.80 mmol) (Wako Pure Chemical Industries, Ltd.) was added thereto, followed by reflux for 3 hours. The mixture was returned to room temperature, and then a saturated aqueous solution of sodium hydrogen carbonate (Wako Pure Chemical Industries, Ltd.) was added thereto, followed by extraction with ethyl acetate (Wako Pure Chemical Industries, Ltd.). The organic layer was dried with anhydrous sodium sulfate (Wako Pure Chemical Industries, Ltd.), and the solvent was distilled off under reduced pressure. The residue was subjected to silica gel column chromatography (chloroform (Wako Pure Chemical Industries, Ltd.) as an eluent), to thereby obtain the title compound (0.27 g, 71% yield).

m.p. 185-188° C.
$^1$H-NMR (CDCl$_3$): δ1.20-3.30 (m, 10H), 7.15-7.60 (m, 12H), 8.44-8.48 (m, 2H).
IR (cm$^{-1}$): 2923, 2811, 1590, 705.

Production Example 11

Synthesis of 1-(triphenylmethyl)succinimide (Compound 11)

[Chem. 22]

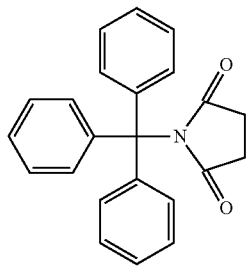

(Compound 11)

Succinimide (0.53 g, 5.35 mmol) (Wako Pure Chemical Industries, Ltd.), triphenylchloromethane (1.49 g, 0.535 mmol) (Wako Pure Chemical Industries, Ltd.), and potassium carbonate (0.74 g, 5.35 mmol) (Wako Pure Chemical Industries, Ltd.) were added to acetonitrile (5 mL) (Wako Pure Chemical Industries, Ltd.), and the mixture was stirred at room temperature overnight. A saturated aqueous solution of sodium hydrogen carbonate (Wako Pure Chemical Industries, Ltd.) was added to the reaction solution, and mixture was extracted with ethyl acetate (Wako Pure Chemical Industries, Ltd.). The organic layer was dried with anhydrous sodium sulfate (Wako Pure Chemical Industries, Ltd.), and the solvent was distilled off under reduced pressure. The residue was subjected to silica gel column chromatography (chloroform) (Wako Pure Chemical Industries, Ltd.), to thereby obtain the title compound (0.48 g, 26% yield).

$^1$H-NMR (CDCl$_3$): δ2.64 (m, 4H), 7.15-7.26 (m, 9H), 7.38-7.41 (m, 6H).

IR (cm$^{-1}$): 2928, 1490, 1455, 707.

Production Example 12

Synthesis of (R)-1-triphenylmethyl-3-pyrrolidinol (Compound 12)

[Chem. 23]

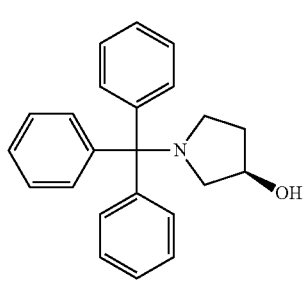

(Compound 12)

(R)-(+)-3-Pyrrolidinol (1.0 g, 11.5 mmol) (Aldrich) and triphenylchloromethane (1.00 g, 3.59 mmol) (Wako Pure Chemical Industries, Ltd.) were dissolved in acetonitrile (30 mL) (Wako Pure Chemical Industries, Ltd.), and the mixture was refluxed for 3 hours. The mixture was allowed to cool to room temperature, and then a saturated aqueous solution of sodium hydrogen carbonate (Wako Pure Chemical Industries, Ltd.) was added to the reaction solution, followed by extraction with ethyl acetate (Wako Pure Chemical Industries, Ltd.). The organic layer was dried with anhydrous sodium sulfate (Wako Pure Chemical Industries, Ltd.), and the solvent was distilled off under reduced pressure. The residue was subjected to silica gel column chromatography (chloroform (Wako Pure Chemical Industries, Ltd.) as an eluent), to thereby obtain the title compound (0.73 g, 62% yield).

m.p. 137-139° C.

$^1$H-NMR (CDCl$_3$): δ1.55-1.82 (m, 2H), 1.93-2.15 (m, 2H), 2.20-2.29 (m, 1H), 2.60-2.85 (m, 2H), 4.25 (brs, 1H), 7.13-7.46 (m, 10H), 7.51-7.52 (m, 5H).

IR (cm$^{-1}$): 3434, 2835, 1447, 710.

Production Example 13

Synthesis of [(naphthyl)phenyl]methanol (Compound 13)

[Chem. 24]

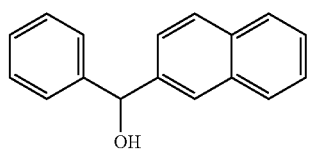

(Compound 13)

A Grignard reagent was prepared from magnesium (0.47 g, 19.6 mmol) (Wako Pure Chemical Industries, Ltd.) and bromobenzene (3.10 g, 19.7 mmol) (Wako Pure Chemical Industries, Ltd.). 2-Naphthaldehyde (2.00 g, 12.8 mmol) (Aldrich) was dissolved in tetrahydrofuran (10 mL) (Wako Pure Chemical Industries, Ltd.), and the Grignard reagent was added thereto, followed by stirring at room temperature for 1 hour. Diluted hydrochloric acid (Wako Pure Chemical Industries, Ltd.) was added to the reaction solution, and mixture was extracted with ethyl acetate (Wako Pure Chemical Industries, Ltd.). The organic layer was dried with anhydrous sodium sulfate (Wako Pure Chemical Industries, Ltd.), and the solvent was distilled off under reduced pressure. The residue was subjected to silica gel column chromatography (chloroform (Wako Pure Chemical Industries, Ltd.) as an eluent), to thereby obtain a ketone derivative which is an intermediate (2.97 g, >1000).

The intermediate (2.97 g, 19.6 mmol) was dissolved in methanol (30 mL) (Wako Pure Chemical Industries, Ltd.), and sodium borohydride (0.83 g, 21.9 mmol) (Wako Pure Chemical Industries, Ltd.) was added thereto, followed by stirring at room temperature for 2 hours. The reaction solution was concentrated under reduced pressure, and then the residue was subjected to silica gel column chromatography (chloroform (Wako Pure Chemical Industries, Ltd.) as an eluent), to thereby obtain the title compound (2.72 g, 91% yield).

$^1$H-NMR (CDCl$_3$): δ2.38 (brs, 1H), 6.00 (s, 1H), 7.20-7.42 (m, 7H), 7.79-7.89 (m, 5H).

Production Example 14

Synthesis of [bis(4-methylphenyl)]methanol (Compound 14)

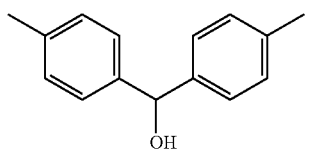
(Compound 14)

With the same method as for Compound 13, 4,4'-dimethylbenzophenone (Wako Pure Chemical Industries, Ltd.) and sodium borohydride (Wako Pure Chemical Industries, Ltd.) were used, to thereby obtain the title compound.

$^1$H-NMR (CDCl$_3$): δ2.31 (s, 6H), 5.76 (s, 1H), 7.12 (d, J=7.8 Hz, 4H), 7.23 (d, J=7.8 Hz, 4H).

Production Example 15

Synthesis of [bis(4-methoxyphenyl)]methanol (Compound 15)

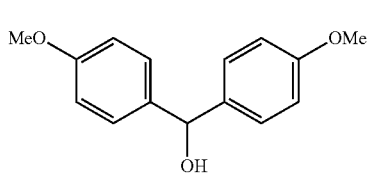
(Compound 15)

With the same method as for Compound 13, 4,4'-dimethoxybenzophenone (Aldrich) and sodium borohydride (Wako Pure Chemical Industries, ltd.) were used, to thereby obtain the title compound.

$^1$H-NMR (CDCl$_3$): 62.10 (s, 1H), 3.79 (s, 6H), 5.75 (s, 1H), 6.86 (dd, J=2.1 Hz, J=15.4 Hz, 4H), 7.27 (dd, J=2.1 Hz, J=15.4 Hz, 4H).

Production Example 16

Synthesis of di(2-pyridyl)phenylmethanol (Compound 16)

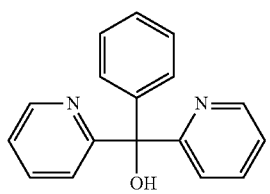
(Compound 16)

With the same method as for Compound 13, a Grignard reagent was prepared from magnesium (Wako Pure Chemical Industries, Ltd.) and bromobenzene (Wako Pure Chemical Industries, Ltd.), and di-2-pyridyl ketone (Aldrich) was allowed to react with the reagent, to thereby obtain the title compound.

$^1$H-NMR (CDCl$_3$): δ1.86 (s, 1H), 7.05-7.37 (m, 7H), 7.64-7.71 (m, 4H), 8.62 (d, J=0.9 Hz, 2H).

IR (cm$^{-1}$): 3397, 1577, 1513, 734.

Production Example 17

Synthesis of [diphenyl(4-methoxyphenyl)]methanol (Compound 17)

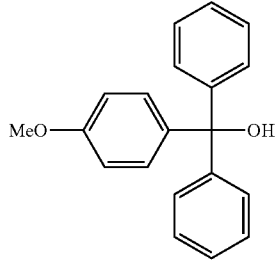
(Compound 17)

With the same method as for Compound 13, a Grignard reagent was prepared from magnesium (Wako Pure Chemical Industries, Ltd.) and parabromoanisole, and benzophenone was allowed to react with the reagent, to thereby obtain the title compound.

m.p. 79-81° C.

$^1$H-NMR (CDCl$_3$): δ 2.75 (s, 1H), 3.79 (s, 3H), 6.82 (dd, J=3.0 Hz, J=9.6 Hz, 2H), 7.2-7.3 (m, 12H).

IR (cm$^{-1}$): 3479, 1607, 1508, 1249.

Production Example 18

Synthesis of [bis(4-methoxyphenyl)phenyl]methanol (Compound 18)

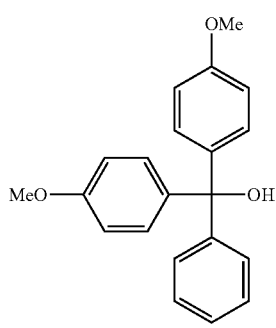
(Compound 18)

With the same method as for Compound 13, a Grignard reagent was prepared from magnesium (Wako Pure Chemical Industries, Ltd.) and bromobenzene, and 4,4'-dimethoxybenzophenone was allowed to react with the reagent, to thereby obtain the title compound.

$^1$H-NMR (CDCl$_3$): δ 3.80 (s, 6H), 6.82 (dd, J=2.7 Hz, J=6.6 Hz, 2H), 7.17 (dd, J=2.1 Hz, J=6.6 Hz, 2H), 7.2-7.3 (m, 9H).

IR (cm$^{-1}$): 3447, 1605, 1506, 1245.

Production Example 19

Synthesis of 1-[[(4-methoxyphenyl)diphenyl]methyl]piperidine (Compound 19)

[Chem. 30]

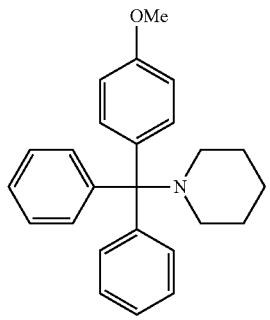
(Compound 19)

[(4-Methoxyphenyl)diphenyl]methyl chloride (0.79 g, 2.56 mmol) (Tokyo Chemical Industry Co., Ltd.) was dissolved in acetonitrile (15 mL) (Wako Pure Chemical Industries, Ltd.), and piperidine (1.20 g, 14.1 mmol) (Wako Pure Chemical Industries, Ltd.) was added thereto. The mixture was refluxed for 1 hour, and then the solvent was distilled off under reduced pressure. A saturated aqueous solution of sodium hydrogen carbonate (Wako Pure Chemical Industries, Ltd.) and water were added to the concentrated residue, and mixture was extracted with ethyl acetate (Wako Pure Chemical Industries, Ltd.). The organic layer was dried with anhydrous sodium sulfate (Wako Pure Chemical Industries, Ltd.), and the solvent was distilled off under reduced pressure. The residue was subjected to alumina column chromatography (n-hexane (Wako Pure Chemical Industries, Ltd.) as an eluent), to thereby obtain the title compound (0.79 g, 86% yield).

m.p. 63-67° C.

$^1$H-NMR (CDCl$_3$): δ 0.70-3.50 (m, 10H), 3.77 (s, 3H), 6.79 (d, J=9.0 Hz, 2H), 7.10-7.6 (m, 12H).

IR (cm$^{-1}$): 2924, 1507, 1441, 712.

Production Example 20

Synthesis of 1-[[bis(4-methoxyphenyl)phenyl]methyl]piperidine (Compound 20)

[Chem. 31]

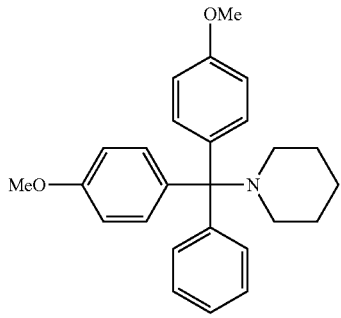
(Compound 20)

4,4'-dimethoxytrityl chloride (0.83 g, 2.45 mmol) (Tokyo Chemical Industry Co., Ltd.) was dissolved in acetonitrile (15 mL) (Wako Pure Chemical Industries, Ltd.), and piperidine (1.24 g, 14.6 mmol) (Wako Pure Chemical Industries, Ltd.) was added thereto. The mixture was refluxed for 1 hour, and the solvent was distilled off under reduced pressure. A saturated aqueous solution of sodium hydrogen carbonate (Wako Pure Chemical Industries, Ltd.) was added to the concentrated residue, and mixture was extracted with ethyl acetate (Wako Pure Chemical Industries, Ltd.). The organic layer was washed with water and brine. After that, the organic layer was dried with anhydrous sodium sulfate (Wako Pure Chemical Industries, Ltd.), and the solvent was distilled off under reduced pressure. The residue was subjected to alumina column chromatography (n-hexane (Wako Pure Chemical Industries, Ltd.)→chloroform (Wako Pure Chemical Industries, Ltd.):n-hexane (Wako Pure Chemical Industries, Ltd.) =1:4 as an eluent), to thereby obtain the title compound (0.81 g, 85% yield).

m.p. 67-70° C.

$^1$H-NMR (CDCl$_3$): 0.70-3.50 (m, 10H), 3.77 (s, 6H), 6.79 (d, J=9.0 Hz, 4H), 7.08-7.53 (m, 9H).

IR (cm$^{-1}$): 2927, 1507, 1249, 1177, 1035.

Production Example 21

Synthesis of 1-[tris(4-methoxyphenyl)methyl]piperidine (Compound 21)

[Chem. 32]

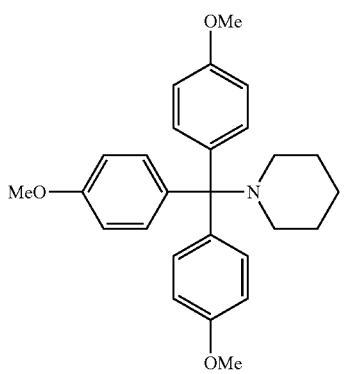
(Compound 21)

4,4',4''-trimethoxytrityl chloride (0.51 g, 1.38 mmol) (Aldrich) was dissolved in acetonitrile (8 mL) (Wako Pure Chemical Industries, Ltd.), and piperidine (0.70 g, 8.22 mmol) (Wako Pure Chemical Industries, Ltd.) was added thereto. The mixture was refluxed for 1 hour, and then the solvent was distilled off under reduced pressure. A saturated aqueous solution of sodium hydrogen carbonate (Wako Pure Chemical Industries, Ltd.) was added to the concentrated residue, and mixture was extracted with ethyl acetate (Wako Pure Chemical Industries, Ltd.). The organic layer was washed with water and brine. After that, the organic layer was dried with anhydrous sodium sulfate (Wako Pure Chemical Industries, Ltd.), and the solvent was distilled off under reduced pressure. The residue was subjected to alumina column chromatography (chloroform (Wako Pure Chemical Industries, Ltd.):n-hexane (Wako Pure Chemical Industries, Ltd.)=1:4 as an eluent), to thereby obtain the title compound (0.28 g, 49% yield).

m.p. 73-75° C.

$^1$H-NMR (CDCl$_3$): 0.70-3.50 (m, 10H), 3.77 (s, 9H), 6.78 (d, J=9.0 Hz, 6H), 7.36 (d, J=7.8 Hz, 6H).

IR (cm$^{-1}$): 2928, 1507, 1249, 1175, 1036.

Production Example 22

Synthesis of tris(4-methylphenyl)methanol (Compound 22)

[Chem. 33]

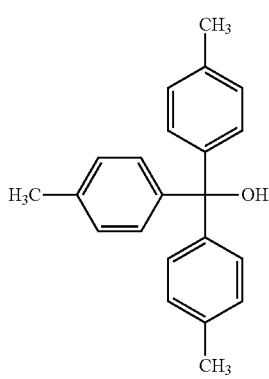

(Compound 22)

A Grignard reagent was prepared from magnesium (0.14 g, 5.76 mmol) (Wako Pure Chemical Industries, Ltd.) and p-bromotoluene (0.48 g, 5.45 mmol) (Wako Pure Chemical Industries, Ltd.). 4,4'-dimethylbenzophenone (0.60 g, 2.85 mmol) (Wako Pure Chemical Industries, Ltd.) was dissolved in tetrahydrofuran (5 mL) (KANTO CHEMICAL CO., INC.), and it was added dropwise to the Grignard reagent while cooling with ice, followed by stirring at room temperature for 4 hours. A saturated aqueous solution of sodium hydrogen carbonate (Wako Pure Chemical Industries, Ltd.) was added to the reaction solution while cooling with ice, and mixture was extracted with ethyl acetate (Wako Pure Chemical Industries, Ltd.). The organic layer was washed with brine. After that, the organic layer was dried with anhydrous sodium sulfate (Wako Pure Chemical Industries, Ltd.), and the solvent was distilled off under reduced pressure. The residue was subjected to silica gel column chromatography (n-hexane (Wako Pure Chemical Industries, Ltd.):ethyl acetate (Wako Pure Chemical Industries, Ltd.)=19:1 as an eluent), to thereby obtain the title compound (0.74 g, 86% yield).

m.p. 91-94° C.

$^1$H-NMR (CDCl$_3$): δ2.33 (s, 9H), 2.68 (s, 1H), 7.08-7.17 (m, 12H).

IR (cm$^{-1}$): 3466, 1510, 1010, 818, 784.

Production Example 23

Synthesis of [bis(4-methylphenyl)phenyl]methanol (Compound 23)

[Chem. 34]

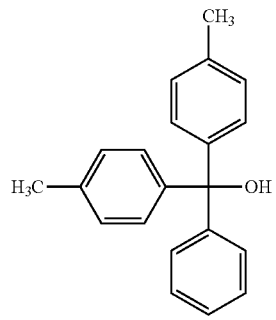

(Compound 23)

With the same method as for Compound 13, a Grignard reagent was prepared from magnesium (Wako Pure Chemical Industries, Ltd.) and bromobenzene (Wako Pure Chemical Industries, Ltd.), and 4,4'-dimethylbenzophenone (Wako Pure Chemical Industries, Ltd.) was allowed to react with the reagent, to thereby obtain the title compound.

m.p. 73-76° C.

$^1$H-NMR (CDCl$_3$): δ2.38 (s, 6H), 2.72 (s, 1H), 7.09-7.17 (m, 8H), 7.26-7.28 (m, 5H).

IR (cm$^{-1}$): 3466, 1510, 1446, 1009, 816, 755, 701.

Production Example 24

Synthesis of [diphenyl(4-methylphenyl)]methanol (Compound 24)

[Chem. 35]

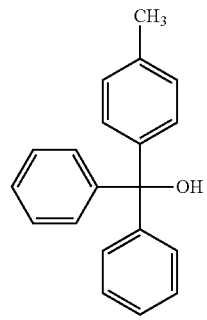

(Compound 24)

With the same method as for Compound 13, a Grignard reagent was prepared from magnesium (Wako Pure Chemical Industries, Ltd.) and p-bromotoluene (Wako Pure Chemical Industries, Ltd.), and benzophenone (Wako Pure Chemical Industries, Ltd.) was allowed to react with the reagent, to thereby obtain the title compound. m.p. 68-71° C.

$^1$H-NMR (CDCl$_3$): δ2.34 (s, 3H), 2.76 (s, 1H), 7.13-7.17 (m, 4H), 7.26-7.32 (m, 10H).

IR (cm$^{-1}$): 3466, 1510, 1445, 1010, 815, 757, 700.

Production Example 25

Synthesis of [[diphenyl(4-methylphenyl)]methyl]piperidine (Compound 25)

[Chem. 36]

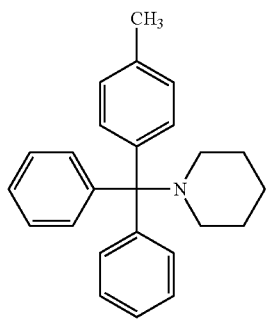

(Compound 25)

Compound 24 described above (0.17 g, 0.620 mmol) was dissolved in chloroform (4 mL) (Wako Pure Chemical Industries, Ltd.), and thionyl chloride (0.5 mL) (Wako Pure Chemical Industries, Ltd.) was added dropwise while cooling with ice. The mixture was returned to room temperature and stirred for 2 hours, and then the solvent was distilled off under reduced pressure, to thereby obtain a residue. The residue was dissolved in acetonitrile (4 mL) (Wako Pure Chemical Industries, Ltd.), and piperidine (0.19 g, 2.23 mmol) (Wako Pure Chemical Industries, Ltd.) was added thereto. The mixture was refluxed for 1 hour and allowed to cool to room temperature. The solvent was distilled off under reduced pressure, and then a saturated aqueous solution of sodium hydrogen carbonate (Wako Pure Chemical Industries, Ltd.) was added to the concentrated residue, and mixture was extracted with ethyl acetate (Wako Pure Chemical Industries, Ltd.). The organic layer was washed with water and brine. After that, the organic layer was dried with anhydrous sodium sulfate (Wako Pure Chemical Industries, Ltd.), and the solvent was distilled off under reduced pressure. The residue was subjected to alumina column chromatography (n-hexane (Wako Pure Chemical Industries, Ltd.) as an eluent), to thereby obtain the title compound (0.18 g, 85% yield).

m.p. 63-67° C.

$^1$H-NMR (CDCl$_3$): δ0.70-3.50 (m, 10H), 2.29 (s, 3H), 7.02-7.18 (m, 4H), 7.19-7.29 (m, 5H), 7.30-7.55 (m, 5H).

IR (cm$^{-1}$): 2922, 2809, 1489, 1447, 711, 701.

Production Example 26

Synthesis of 1-[[bis(4-methylphenyl)phenyl]methyl]piperidine (Compound 26)

[Chem. 37]

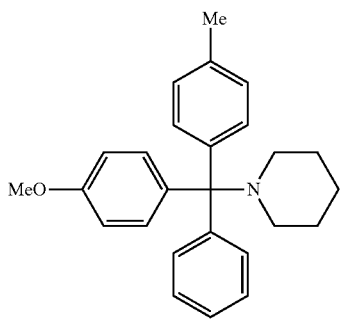

(Compound 26)

Compound 23 described above (0.17 g, 0.589 mmol) was dissolved in chloroform (4 mL) (Wako Pure Chemical Industries, Ltd.), and thionyl chloride (0.5 mL) (Wako Pure Chemical Industries, Ltd.) was added dropwise while cooling with ice. The mixture was returned to room temperature and stirred for 1 hour, and then the solvent was distilled off under reduced pressure, to thereby obtain a residue. The residue was dissolved in acetonitrile (4 mL) (Wako Pure Chemical Industries, Ltd.), and piperidine (0.19 g, 2.23 mmol) (Wako Pure Chemical Industries, Ltd.) was added thereto. The mixture was refluxed for 45 minutes and allowed to cool to room temperature. The solvent was distilled off under reduced pressure, and then a saturated aqueous solution of sodium hydrogen carbonate (Wako Pure Chemical Industries, Ltd.) was added to the concentrated residue, and mixture was extracted with ethyl acetate (Wako Pure Chemical Industries, Ltd.). The organic layer was washed with water and brine. After that, the organic layer was dried with anhydrous sodium sulfate (Wako Pure Chemical Industries, Ltd.), and the solvent was distilled off under reduced pressure. The residue was subjected to alumina column chromatography (n-hexane (Wako Pure Chemical Industries, Ltd.) as an eluent), to thereby obtain the title compound (0.17 g, 81% yield).

m.p. 68-71° C.

$^1$H-NMR (CDCl$_3$): δ0.70-3.50 (m, 10H), 2.29 (s, 6H), 7.04-7.46 (m, 13H).

IR (cm$^{-1}$): 2922, 1507, 1445, 752, 723.

Production Example 27

Synthesis of 1-[tris(4-methylphenyl)methyl]piperidine (Compound 27)

[Chem. 38]

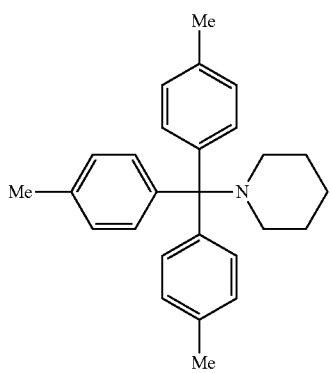

(Compound 27)

Compound 22 described above (0.17 g, 0.562 mmol) was dissolved in chloroform (4 mL) (Wako Pure Chemical Industries, Ltd.), and thionyl chloride (0.5 mL) (Wako Pure Chemical Industries, Ltd.) was added dropwise while cooling with ice. The mixture was returned to room temperature and stirred for 2 hours, and then the solvent was distilled off under reduced pressure, to thereby obtain a residue. The residue was dissolved in acetonitrile (4 mL) (Wako Pure Chemical Industries, Ltd.), and piperidine (0.19 g, 2.23 mmol) (Wako Pure Chemical Industries, Ltd.) was added thereto. The mixture was refluxed for 1 hour and allowed to cool to room temperature. The solvent was distilled off under reduced pressure, and then a saturated aqueous solution of sodium hydrogen carbonate (Wako Pure Chemical Industries, Ltd.) was added to the concentrated residue, and mixture was extracted with ethyl acetate (Wako Pure Chemical Industries, Ltd.). The organic layer was washed with water and brine. After that, the organic layer was dried with anhydrous sodium sulfate (Wako Pure Chemical Industries, Ltd.), and the solvent was distilled off under reduced pressure. The residue was subjected to alumina column chromatography (n-hexane (Wako Pure Chemical Industries, Ltd.) as an eluent), to thereby obtain the title compound (0.19 g, 92% yield).

$^1$H-NMR (CDCl$_3$): δ0.70-3.50 (m, 10H), 2.28 (s, 9H), 7.04 (d, J=8.4 Hz, 6H), 7.23-7.40 (m, 6H).

IR (cm$^{-1}$): 2922, 1508, 1185, 807, 781, 569.

Production Example 28

Synthesis of 1-(diphenylmethyl)pyrrolidine (Compound 28)

[Chem. 39]

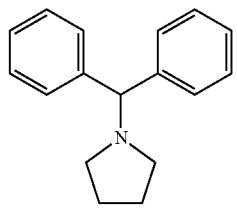

(Compound 28)

Chlorodiphenylmethane (0.50 g, 2.47 mmol) (Wako Pure Chemical Industries, Ltd.), pyrrolidine (0.53 g, 7.45 mmol) (Tokyo Chemical Industry Co., Ltd.), and potassium iodide (0.10 g, 0.60 mmol) (Wako Pure Chemical Industries, Ltd.) were added to acetonitrile (20 mL) (Wako Pure Chemical Industries, Ltd.), and the mixture was refluxed for 2 hours. The mixture was allowed to cool to room temperature. After that, a saturated aqueous solution of sodium hydrogen carbonate (Wako Pure Chemical Industries, Ltd.) was added to the reaction solution, and mixture was extracted with ethyl acetate (Wako Pure Chemical Industries, Ltd.). The organic layer was dried with anhydrous sodium sulfate (Wako Pure Chemical Industries, Ltd.), and the solvent was distilled off under reduced pressure. The residue was subjected to silica gel column chromatography (chloroform (Wako Pure Chemical Industries, Ltd.):methanol (Wako Pure Chemical Industries, Ltd.)=99:1 as an eluent), to thereby obtain the title compound (0.36 g, 61% yield).

m.p. 69-72° C.

$^1$H-NMR (CDCl$_3$): δ1.73-1.79 (m, 4H), 2.40-2.44 (m, 4H), 4.15 (s, 1H), 7.12-7.47 (m, 10H).

IR (cm$^{-1}$): 2793, 1452, 703.

Production Example 29

Synthesis of 1-[bis(4-methylphenyl)methyl]pyrrolidine (Compound 29)

[Chem. 40]

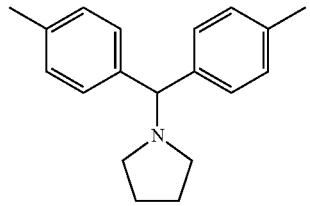

(Compound 29)

Compound 14 (0.30 g, 1.41 mmol) was dissolved in thionyl chloride (1 mL) (Wako Pure Chemical Industries, Ltd.), and the mixture was refluxed for 2 hours. The reaction solution was concentrated under reduced pressure, to thereby obtain a residue. The residue was dissolved in acetonitrile (5 mL)

(Wako Pure Chemical Industries, Ltd.), and pyrrolidine (0.50 g, 7.03 mmol) was added thereto, and the mixture was refluxed for 2 hours and then allowed to cool to room temperature. A saturated aqueous solution of sodium hydrogen carbonate (Wako Pure Chemical Industries, Ltd.) was added to the reaction solution, and then mixture was extracted with ethyl acetate. The organic layer was dried with anhydrous sodium sulfate (Wako Pure Chemical Industries, Ltd.), and the solvent was distilled off under reduced pressure. The residue was subjected to silica gel column chromatography (chloroform (Wako Pure Chemical Industries, Ltd.):methanol (Wako Pure Chemical Industries, Ltd.)=99:1 as an eluent), to thereby obtain the title compound (0.32 g, 84% yield).

m.p. 61-63° C.

$^1$H-NMR (CDCl$_3$): δ1.74-1.78 (m, 4H), 2.40 (s, 6H), 2.35-2.45 (m, 4H), 4.01 (s, 1H), 7.05 (d, J=7.8 Hz, 4H), 7.32 (d, J=7.8 Hz, 4H). IR (cm$^{-1}$): 2962, 2802, 1509, 721.

Production Example 30

Synthesis of N-(triphenylmethyl)-N-ethylamine (Compound 30)

[Chem. 41]

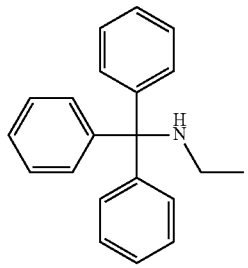

(Compound 30)

Triphenylmethylamine (1.00 g, 3.86 mmol) (Wako Pure Chemical Industries, Ltd.) and iodoethane (1.50 g, 9.62 mmol) (Wako Pure Chemical Industries, Ltd.) were dissolved in acetonitrile (5 mL) (Wako Pure Chemical Industries, Ltd.), and the mixture was left to stand still at room temperature for 3 days. The solvent was distilled off under reduced pressure, and the residue was subjected to silica gel column chromatography (chloroform (Wako Pure Chemical Industries, Ltd.) as an eluent), to thereby obtain the title compound (0.31 g, 28% yield).

m.p. 75-77° C.

$^1$H-NMR (CDCl$_3$): δ1.06 (t, J=6.9 Hz, 3H), 1.98 (t, J=6.9 Hz, 2H), 7.13-7.45 (m, 15H).

Production Example 31

Synthesis of 2-[[diphenyl(4-methoxyphenyl)]methyloxy]ethanol (Compound 31)

[Chem. 42]

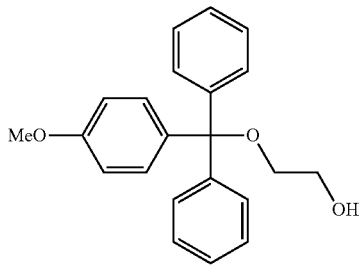

(Compound 31)

Ethylene glycol (1.00 g, 16.1 mmol) (Wako Pure Chemical Industries, Ltd.), 4-methoxytriphenyl chloride (1.00 g, 3.23 mmol) (Wako Pure Chemical Industries, Ltd.), and triethylamine (0.89 g, 8.81 mmol) (Wako Pure Chemical Industries, Ltd.) were dissolved in methylene chloride (50 mL) (Wako Pure Chemical Industries, Ltd.), and the mixture was stirred at room temperature overnight. Water (50 mL) was added to reaction solution, and mixture was extracted with methylene chloride (Wako Pure Chemical Industries, Ltd.). The organic layer was dried with anhydrous sodium sulfate (Wako Pure Chemical Industries, Ltd.), and the solvent was distilled off under reduced pressure. The residue was subjected to silica gel column chromatography (chloroform (Wako Pure Chemical Industries, Ltd.) as an eluent), to thereby obtain the title compound (0.91 g, 84% yield).

$^1$H-NMR (CDCl$_3$): δ3.25 (d, J=5.1 Hz, 2H), 3.78 (d, J=5.1 Hz, 2H), 3.79 (s, 3H), 6.83 (d, J=9.0 Hz, 2H), 7.25-7.54 (m, 12H).

IR (cm$^{-1}$): 3419, 1607, 1509, 1251.

Production Example 32

Synthesis of 2-[bis(4-methoxyphenyl)phenylmethyloxy]ethanol (Compound 32)

[Chem. 43]

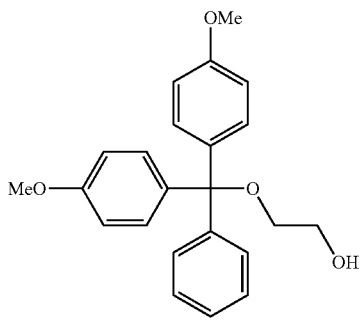

(Compound 32)

Ethylene glycol (0.92 g, 14.8 mmol) (Wako Pure Chemical Industries, Ltd.), 4,4'-dimethoxytrityl chloride (1.00 g, 2.95 mmol) (Wako Pure Chemical Industries, Ltd.), and triethylamine (0.89 g, 8.81 mmol) (Wako Pure Chemical Industries, Ltd.) were dissolved in methylene chloride (25 mL) (Wako Pure Chemical Industries, Ltd.), and the mixture was stirred at room temperature overnight. Water (50 mL) was added to reaction solution, and mixture was extracted with methylene chloride (Wako Pure Chemical Industries, Ltd.). The organic layer was dried with anhydrous sodium sulfate (Wako Pure Chemical Industries, Ltd.), and the solvent was distilled off under reduced pressure. The residue was subjected to silica gel column chromatography (chloroform (Wako Pure Chemical Industries, Ltd.) as an eluent), to thereby obtain the title compound (0.51 g, 47% yield).

$^1$H-NMR (DMSO): δ3.25 (t, J=5.1 Hz, 2H), 3.79 (t, J=5.1 Hz, 2H), 3.79 (m, 6H), 6.83 (dd, J=2.4 Hz, J=6.9 Hz, 4H), 7.13-7.45 (m, 9H). IR (cm$^{-1}$): 3398, 1607, 1510, 1251.

Production Example 33

Synthesis of 2-[[diphenyl(4-methoxyphenyl)]methylamino]ethanol (Compound 33)

[Chem. 44]

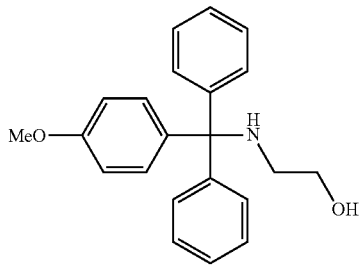

(Compound 33)

4-Methoxytrityl chloride (2.77 g, 9.00 mmol) (Wako Pure Chemical Industries, Ltd.) and aminoethanol (2.74 g, 44.9 mmol) (Wako Pure Chemical Industries, Ltd.) were dissolved in acetonitrile (50 mL) (Wako Pure Chemical Industries, Ltd.), and the mixture was stirred at room temperature overnight. Ethyl acetate (Wako Pure Chemical Industries, Ltd.) and water were added thereto, and mixture was extracted. The organic layer was dried with anhydrous sodium sulfate (Wako Pure Chemical Industries, Ltd.), and the solvent was distilled off under reduced pressure. The residue was subjected to silica gel column chromatography (chloroform (Wako Pure Chemical Industries, Ltd.) as an eluent), to thereby obtain the title compound (2.01 g, 67% yield).

$^1$H-NMR (CDCl$_3$): δ2.36 (t, J=5.1 Hz, 2H), 3.68 (t, J=5.1 Hz, 2H), 3.80 (s, 3H), 6.81 (d, J=9.0 Hz, 2H), 7.23-7.55 (m, 12H).

IR (cm$^{-1}$): 3323, 1609, 1508, 1249.

Production Example 34

Synthesis of 2-[[bis(4-methoxyphenyl)phenyl]methylamino]ethanol (Compound 34)

[Chem. 45]

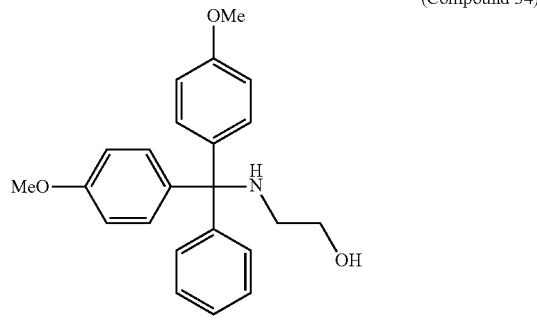

(Compound 34)

4,4'-dimethoxytrityl chloride (0.50 g, 1.48 mmol) (Wako Pure Chemical Industries, Ltd.) and aminoethanol (0.27 g, 4.42 mmol) (Wako Pure Chemical Industries, Ltd.) were dissolved in acetonitrile (20 mL) (Wako Pure Chemical Industries, Ltd.), and the mixture was stirred at room temperature overnight. Ethyl acetate (Wako Pure Chemical Industries, Ltd.) and water were added thereto, and mixture was extracted. The organic layer was dried with anhydrous sodium sulfate (Wako Pure Chemical Industries, Ltd.), and the solvent was distilled off under reduced pressure. The residue was subjected to silica gel column chromatography (chloroform (Wako Pure Chemical Industries, Ltd.) as an eluent), to thereby obtain the title compound (0.43 g, 80% yield).

$^1$H-NMR (CDCl$_3$): δ2.87 (t, J=5.1 Hz, 2H), 3.14 (t, J=5.1 Hz, 2H), 3.79 (s, 6H), 6.82 (dd, J=2.7 Hz, J=6.9 Hz, 4H), 7.21-7.56 (m, 9H).

IR (cm$^{-1}$): 3380, 1609, 1177.

Production Example 35

Synthesis of 2-[[diphenyl(4-methoxyphenyl)]methyloxy]ethylamine (Compound 35)

[Chem. 46]

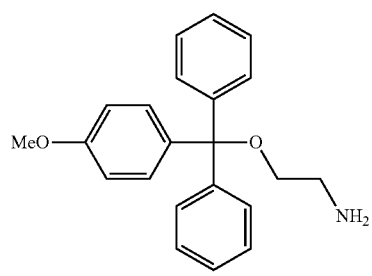

(Compound 35)

4-Methoxytrityl chloride (2.00 g, 6.48 mmol) (Wako Pure Chemical Industries, Ltd.), 1-(2-trityloxyethyl)piperidine-2,5-dione (1.24 g, 6.48 mmol) (Wako Pure Chemical Industries, Ltd.), and triethylamine (1.96 g, 19.4 mmol) (Wako Pure Chemical Industries, Ltd.) were dissolved in methylene chloride (30 mL) (Wako Pure Chemical Industries, Ltd.), and the mixture was stirred at room temperature overnight. The mixture was poured into a mixed solution of methylene chloride (Wako Pure Chemical Industries, Ltd.) and diluted hydrochloric acid (Wako Pure Chemical Industries, Ltd.), and the mixture was shaken, followed by separation of the organic layer. The organic layer was dried with anhydrous sodium sulfate (Wako Pure Chemical Industries, Ltd.), and then suction-filtered and concentrated under reduced pressure. The residue was subjected to silica gel column chromatography (chloroform (Wako Pure Chemical Industries, Ltd.) as an eluent), to thereby obtain an intermediate (2.67 g, 89% yield).

The intermediate (0.50 g, 1.10 mmol) was dissolved in methanol (10 mL) (Wako Pure Chemical Industries, Ltd.), and hydrazine (2 mL) (Wako Pure Chemical Industries, Ltd.) was added thereto, followed by stirring at room temperature for 1 hour. The solvent was distilled off under reduced pressure, and then the residue was added to a mixed solution of chloroform (Wako Pure Chemical Industries, Ltd.) and a saturated aqueous solution of sodium hydrogen carbonate (Wako Pure Chemical Industries, Ltd.). The mixture was shaken, and then the organic layer was separated. The organic layer was dried with anhydrous sodium sulfate (Wako Pure Chemical Industries, Ltd.), and then suction-filtered and concentrated under reduced pressure. The residue was subjected to silica gel column chromatography (chloroform (Wako Pure Chemical Industries, Ltd.):methanol (Wako Pure Chemical Industries, Ltd.)=9:1 as an eluent), to thereby obtain the title compound (0.20 g, 57% yield).

$^1$H-NMR (CDCl$_3$): δ2.87 (t, J=5.4 Hz, 2H), 3.16 (t, J=5.4 Hz, 2H), 3.79 (s, 3H), 6.83 (dd, J=2.1 Hz, J=6.9 Hz, 2H), 7.21-7.56 (m, 12H).

IR (cm$^{-1}$): 3385, 1607, 1510, 1251.

Production Example 36

Synthesis of 2-[[bis(4-methoxyphenyl)phenyl]methyloxy]ethylamine (Compound 36)

[Chem. 47]

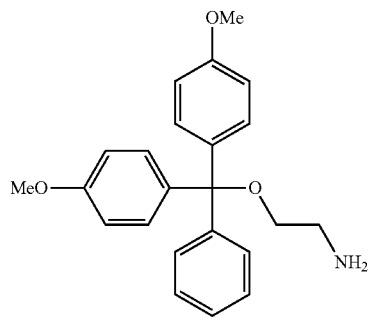

(Compound 36)

4,4'-dimethoxytrityl chloride (1.00 g, 2.95 mmol) (Wako Pure Chemical Industries, Ltd.), 1-(2-trityloxyethyl)pyrrolidine-2,5-dione (0.57 g, 3.00 mmol) (Wako Pure Chemical Industries, Ltd.), and triethylamine (0.89 g, 8.81 mmol) (Wako Pure Chemical Industries, Ltd.) were dissolved in methylene chloride (20 mL) (Wako Pure Chemical Industries, Ltd.), and the mixture was stirred at room temperature overnight. The mixture was poured into a mixed solution of methylene chloride (Wako Pure Chemical Industries, Ltd.) and diluted hydrochloric acid (Wako Pure Chemical Industries, Ltd.), and the mixture was shaken, followed by separation of the organic layer. The organic layer was dried with anhydrous sodium sulfate (Wako Pure Chemical Industries, Ltd.), and then suction-filtered and concentrated under reduced pressure. The residue was subjected to silica gel column chromatography (chloroform (Wako Pure Chemical Industries, Ltd.) as an eluent), to thereby obtain an intermediate (0.93 g, 64% yield).

The intermediate (0.93 g, 1.88 mmol) was dissolved in methanol (25 mL) (Wako Pure Chemical Industries, Ltd.), and hydrazine (4 mL) (Wako Pure Chemical Industries, Ltd.) was added thereto, followed by stirring at room temperature for 1 hour. The solvent was distilled off under reduced pressure, and then the residue was added to a mixed solution of chloroform (Wako Pure Chemical Industries, Ltd.) and a saturated aqueous solution of sodium hydrogen carbonate (Wako Pure Chemical Industries, Ltd.). The mixture was shaken, and then the organic layer was separated. The organic layer was dried with anhydrous sodium sulfate (Wako Pure Chemical Industries, Ltd.), and then suction-filtered and concentrated under reduced pressure. The residue was subjected to silica gel column chromatography (chloroform (Wako Pure Chemical Industries, Ltd.):methanol (Wako Pure Chemical Industries, Ltd.)=9:1 as an eluent), to thereby obtain the title compound (0.33 g, 49% yield).

$^1$H-NMR (CDCl$_3$): δ2.85 (t, J=5.1 Hz, 2H), 3.13 (t, J=5.1 Hz, 2H), 3.79 (s, 6H), 6.81 (d, J=9.0 Hz, 4H), 7.36-7.53 (m, 9H).

IR (cm$^{-1}$): 3385, 1608, 1508, 1176.

Production Example 37

Synthesis of N,N-[bis(2-hydroxyethyl)]-N-(triphenylmethyl)amine (Compound 37)

[Chem. 48]

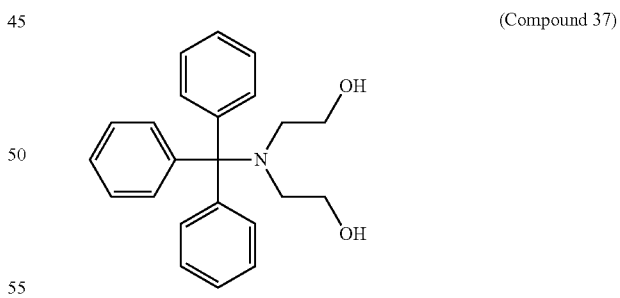

(Compound 37)

A solution of triphenylchloromethane (2.01 g, 7.20 mmol) (Wako Pure Chemical Industries, Ltd.) in methylene chloride (12 mL) (Wako Pure Chemical Industries, Ltd.) was added dropwise over 20 minutes to a solution of diethanolamine (1.67 g, 15.9 mmol) (Wako Pure Chemical Industries, Ltd.) in N,N-dimethylformamide (13 mL) (Wako Pure Chemical Industries, Ltd.) while stirring and cooling with ice. The mixture was returned to room temperature and stirred overnight, and then diethyl ether (Wako Pure Chemical Industries, Ltd.) and water were added thereto, followed by extraction.

The organic layer was dried with anhydrous sodium sulfate (Wako Pure Chemical Industries, Ltd.), and the solvent was distilled off under reduced pressure. The residue was recrystallized from chloroform (Wako Pure Chemical Industries, Ltd.)/n-hexane (Wako Pure Chemical Industries, Ltd.), to thereby obtain the title compound (1.24 g, 49% yield).

m.p. 159-160° C.

$^1$H-NMR (CDCl$_3$): δ2.58 (t, J=6.3 Hz, 4H), 3.78 (t, J=6.3 Hz, 4H), 7.13-7.31 (m, 9H), 7.58-7.62 (m, 6H).

Production Example 38

Synthesis of 1,2-dihydroxy-3-(triphenylmethyloxy)propane (Compound 38)

[Chem. 49]

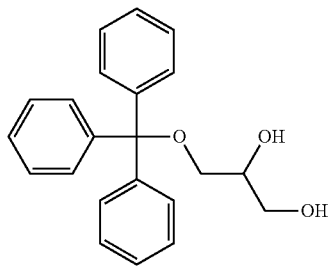

(Compound 38)

Glycerol (3.02 g, 32.8 mmol) (Wako Pure Chemical Industries, Ltd.) and triphenylchloromethane (1.00 g, 3.50 mmol) (Wako Pure Chemical Industries, Ltd.) were dissolved in pyridine (20 mL) (Wako Pure Chemical Industries, Ltd.), and the mixture was refluxed for 5 hours. The mixture was allowed to cool to room temperature, and then water was added thereto, followed by extraction with ethyl acetate (Wako Pure Chemical Industries, Ltd.). The organic layer was dried with anhydrous sodium sulfate (Wako Pure Chemical Industries, Ltd.), and the solvent was distilled off under reduced pressure. The residue was subjected to silica gel column chromatography (chloroform (Wako Pure Chemical Industries, Ltd.):methanol (Wako Pure Chemical Industries, Ltd.)=97:3), to thereby obtain the title compound (0.50 g, 42% yield).

m.p. 108-110° C.

$^1$H-NMR (CDCl$_3$): δ 3.22-3.34 (m, 2H), 3.54-3.81 (m, 2H), 3.8.5-3.99 (m, 1H), 7.22-7.54 (m, 15H).

Production Example 39

Synthesis of N-(triphenylmethyl) serine (Compound 39)

[Chem. 50]

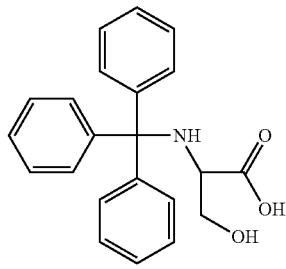

(Compound 39)

L-Serine (2.10 g, 20.0 mmol) (Wako Pure Chemical Industries, Ltd.) was dissolved in methylene chloride (20 mL) (Wako Pure Chemical Industries, Ltd.), and then trimethylsilyl chloride (8.9 mL) (Shin-Etsu Chemical Co., Ltd.) was added thereto, followed by reflux for 20 minutes. The mixture was returned to room temperature, and then triethylamine (10 mL) (Wako Pure Chemical Industries, Ltd.) was added thereto, followed by reflux for 45 minutes. The mixture was ice-cooled, and then triethylamine (2.8 mL) (Wako Pure Chemical Industries, Ltd.) and triphenylchloromethane (5.61 g, 20.1 mmol) (Wako Pure Chemical Industries, Ltd.) were added thereto, followed by stirring at room temperature for 5 hours. An excessive amount of methanol (Wako Pure Chemical Industries, Ltd.) was added to the reaction solution, and the mixture was concentrated under reduced pressure. The organic layer was dried with anhydrous sodium sulfate (Wako Pure Chemical Industries, Ltd.), and the solvent was distilled off under reduced pressure. The residue was subjected to silica gel column chromatography (chloroform (Wako Pure Chemical Industries, Ltd.):methanol (Wako Pure Chemical Industries, Ltd.)=99:1 as an eluent), to thereby obtain the title compound (0.36 g, 5% yield).

$^1$H-NMR (CDCl$_3$): δ2.83-2.92 (m, 2H), 3.51 (m, 1H), 3.67-3.77 (m, 1H), 7.20-7.44 (m, 15H).

Production Example 40

Synthesis of 1-[(diphenylpyridyl)methyl]imidazole (Compound 40)

[Chem. 51]

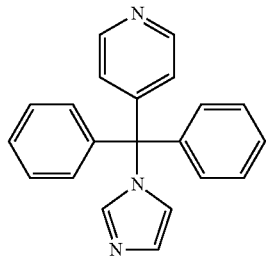

(Compound 40)

Compound 9 described above (0.35 g, 1.34 mmol) was dissolved in thionyl chloride (2 mL) (Wako Pure Chemical Industries, Ltd.), and the mixture was refluxed for 30 minutes. The reaction solution was allowed to cool to room temperature, and then the solvent was distilled off under reduced pressure. The residue was dissolved in acetonitrile (30 mL) (Wako Pure Chemical Industries, Ltd.) and imidazole (1.50 g, 2.20 mmol) was added thereto, followed by reflux for 3 hours. The reaction solution was allowed to cool to room temperature, and then water and ethyl acetate (Wako Pure Chemical Industries, Ltd.) were added thereto. The mixture was shaken, and then the organic layer was separated. The organic layer was dried with anhydrous sodium sulfate (Wako Pure Chemical Industries, Ltd.) and suction-filtered, and then the solvent was distilled off under reduced pressure. The residue was subjected to silica gel column chromatography (chloroform (Wako Pure Chemical Industries, Ltd.) chloroform (Wako Pure Chemical Industries, Ltd.):methanol (Wako Pure Chemical Industries, Ltd.)=99:1 as an eluent), to thereby obtain the title compound (266 g, 62% yield).

m.p. 210-212° C.

$^1$H-NMR (CDCl$_3$): δ6.80 (d, 1H, J=1.2 Hz), 7.07-7.14 (m, 7H), 7.35-7.38 (m, 6H), 7.45 (t, 1H, J=1.2 Hz), 8.62 (dd, 2H, J=1.5 Hz, J=4.5 Hz)

Production Example 41

Synthesis of 1-[bis(methylphenyl)methyl]imidazole (Compound 41)

[Chem. 52]

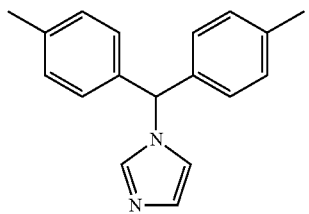

(Compound 41)

With the same method as for Compound 40, Compound 14 described above, thionyl chloride (Wako Pure Chemical Industries, Ltd.), and imidazole (Wako Pure Chemical Industries, Ltd.) were used, to thereby obtain the title compound.

$^1$H-NMR (CDCl$_3$): δ2.35 (s, 6H), 6.44 (s, 1H), 6.83 (t, 1H, J=1.2 Hz), 6.98 (d, 4H, 8.1 Hz), 7.15 (d, 4H, J=8.1 Hz), 7.27 (s, 1H), 7.39 (s, 1H)

EXAMPLES

Hereinafter, the present invention is described in more detail by way of examples. However, it goes without saying that the present invention is not limited only to these examples.

Test Example 1

Melanin Production Inhibition Test using Cultured Normal Human Melanocytes

The inhibitory effect on melanin production of Compound 1 was evaluated using 2-thiouracil ($^{14}$C-labeled 2-thiouracil was used in this test) which is incorporated specifically into melanin in an intracellular melanin synthesis process. Complete medium for culture of melanocytes (manufactured by Kurabo Industries Ltd.) was added to 15 wells in a 24-well plate in an amount of 2 mL per well, and normal human melanocytes (manufactured by Kurabo Industries Ltd.) were seeded into the wells at a concentration of 1.5×10$^4$ cells/cm$^2$. The cells were cultured in a 5% carbon dioxide atmosphere at 37° C. for 24 hours. Thereafter, the medium in all the wells was exchanged under the following conditions: fresh complete medium for culture of melanocytes (control) was used in three wells; each of complete medium for culture of melanocytes, which including Compound 1 at concentrations of 1.0 μM, 2.0 μM, and 4.0 μM, was used in a total of nine wells including three wells for each concentration; and complete medium for culture of melanocytes, each of which including arbutin (positive control) known as a melanin production inhibitor at a concentration of 0.5 mM (500 μM), was used in the other three wells. Further, 2-[2-$^{14}$C]thiouracil ($^{14}$C-labeled thiouracil) was added to each of these 15 wells at 0.25×10$^{-6}$ Ci (curie). Then, the cells were cultured for further 3 days under the same conditions as the above. After the completion of culture, the culture medium was removed from the wells, and the cells were washed with phosphate buffered physiological saline (PBS) and then separated from the bottoms of the wells with medium including trypsin and EDTA to prepare cell suspensions, followed by centrifugation to collect the cells. The number of the cells was counted using a hemocytometer. Thereafter, the amounts of $^{14}$C-thiouracil in the cells collected from each well (0.25×10$^{-6}$ Ci) were measured using a liquid scintillation counter (ALOKA CO., LTD.). The percentages of an amount of radioactivity in the cells cultured in the medium including the test substances with respect to an amount of radioactivity in the cells collected from the well of the control were calculated as amounts of melanin (%). That is, as the amount of radioactivity incorporated into the cells is smaller, the amount of melanin is evaluated to be smaller, i.e., the melanin inhibition effect of the component added is evaluated to be larger.

TABLE 1

| Component added to medium | Addition amount (μM) | Amount of melanin (%) |
|---|---|---|
| Compound 1 | 1.0 | 63.8 ± 3.6 |
|  | 2.0 | 37.0 ± 5.3 |
|  | 4.0 | 29.2 ± 2.9 |
| Arbutin | 500 | 64.6 ± 2.3 |

* The rate when the average radioactivity of the control is defined as 100% is shown as the amount of melanin. The amount of melanin shows a mean ± standard deviation of three samples.

The results shown in Table 1 reveal that Compound 1 has a concentration-dependent inhibitory effect on melanin production. Further, comparison with arbutin known as a melanin production inhibitor suggests that the inhibitory effects of melanin production of 0.5 mM arbutin and 1.0 μM Compound 1 are almost the same. The results show that the inhibitory effect of melanin production of Compound 1 is 100 times or more that of arbutin.

Test Example 2

Melanin Production Inhibition Tests of Compounds 2 to 39

Inhibitory effects on melanin production of Compounds 2 to 39 (however, the effects of Compound 9 and 15 were not measured) were examined in the same procedure as in Test Example 1. The concentrations of the compounds added were adjusted so that the compounds did not inhibit proliferation of cells, and the compounds were used for the tests. Table 2 shows the results. Table 2 reveals that Compounds 2 to 39 have excellent inhibitory effects on melanin production although the potencies of the effects of the compounds are different.

TABLE 2

| Component added to medium (Compound No.) | Addition amount (μM) | Amount of melanin (%) |
|---|---|---|
| 2 | 5.0 | 44.0 ± 3.2 |
| 3 | 5.0 | 51.6 ± 4.2 |
| 4 | 2.0 | 33.8 ± 0.8 |
| 5 | 1.5 | 37.7 ± 0.8 |
| 6 | 2.0 | 32.6 ± 4.1 |
| 7 | 6.0 | 51.1 ± 5.8 |
| 8 | 2.5 | 39.2 ± 10.7 |
| 10 | 0.3 | 77.3 ± 0.4 |
| 11 | 15 | 53.7 ± 0.9 |
| 12 | 5.0 | 62.9 ± 3.7 |
| 13 | 20 | 68.7 ± 5.2 |
| 14 | 25 | 44.6 ± 5.6 |
| 16 | 100 | 91.5 ± 4.6 |
| 17 | 10 | 37.0 ± 1.5 |
| 18 | 10 | 55.3 ± 3.4 |
| 19 | 3.1 | 51.5 ± 5.7 |
| 20 | 3.1 | 73.2 ± 3.2 |
| 21 | 12.5 | 53.5 ± 0.4 |
| 22 | 1.6 | 50.6 ± 2.0 |
| 23 | 3.1 | 47.2 ± 0.2 |
| 24 | 3.1 | 51.6 ± 1.6 |
| 25 | 1.6 | 48.0 ± 1.9 |
| 26 | 1.6 | 38.4 ± 2.5 |
| 27 | 3.1 | 47.5 ± 0.6 |
| 28 | 60 | 77.3 ± 5.6 |
| 29 | 20 | 49.0 ± 1.9 |
| 30 | 8.0 | 41.4 ± 0.7 |
| 31 | 3.1 | 37.6 ± 3.3 |
| 32 | 3.1 | 58.8 ± 7.1 |
| 33 | 5.0 | 67.7 ± 5.1 |
| 34 | 5.0 | 71.4 ± 1.9 |
| 35 | 5.0 | 80.4 ± 8.8 |
| 36 | 10 | 71.7 ± 5.1 |
| 37 | 4.0 | 69.6 ± 3.9 |
| 38 | 8.0 | 75.6 ± 0.2 |
| 39 | 8.0 | 54.9 ± 5.5 |

* The rate when the average radioactivity of the control is defined as 100% is shown as the amount of melanin. The amount of melanin shows a mean ± standard deviation of three samples.

Test Example 3

Melanin Production Inhibition Tests of Other Compounds

Inhibitory effects on melanin production of the compounds are shown in Table 3. These were examined in the same procedure as in Test Example 1. The concentrations, of the compounds added were adjusted so that the compounds did not inhibit proliferation of cells, and the compounds were used for the tests. Table 3 shows the results. Table 3 reveals that the compounds also have excellent inhibitory effects on melanin production although the potencies of the effects of the compounds are different.

TABLE 3

| Component added to medium | Addition amount (μM) | Amount of melanin (%) |
|---|---|---|
| Aminodiphenylmethane (Tokyo Chemical Industry Co., Ltd.) | 40 | 36.6 ± 12.8 |

TABLE 3-continued

| Component added to medium | Addition amount (μM) | Amount of melanin (%) |
|---|---|---|
| Triphenylmethylamine (Wako Pure Chemical Industries, Ltd.) | 12.5 | 57.3 ± 1.6 |
| Triphenylmethanol (Wako Pure Chemical Industries, Ltd.) | 7.5 | 41.3 ± 2.8 |
| Triphenylmethane (Wako Pure Chemical Industries, Ltd.) | 10 | 42.3 ± 1.4 |
| 4,4'-(1-Phenylidene)-bisphenol (Aldrich) | 3.0 | 44.8 ± 1.0 |
| 4,4'-Ethylidenebisphenol (Aldrich) | 25 | 30.5 ± 6.1 |
| 4-Tritylphenol (Wako Pure Chemical Industries, Ltd.) | 1.25 | 27.0 ± 0.4 |
| 4,4'-Cyclohexylidenebisphenol (Aldrich) | 3.0 | 38.3 ± 2.5 |

* The rate when the average radioactivity of the control is defined as 100% is shown as the amount of melanin. The amount of melanin shows a mean ± standard deviation of three samples.

Test Example 4

Ultraviolet Ray-Induced Pigmentation Inhibition Test Using Pigmented Guinea Pigs The hair of the dorsal skin of each of eight pigmented guinea pigs was removed and shaved using an electrical hair clipper and shaver, and each of the sites was covered with a black cloth having a total of four (two on the top and bottom and two on the right and left) irradiation windows with a size of 2×2 cm, and then irradiated with ultraviolet rays of 300 mJ/cm$^2$ using FL20S•E30 lamp as a light source. This operation was repeated on days 1, 3, 5, 8, 10, and 12 after the start of the test to induce pigmentation on the four test sites.

Compound 2, Compound 3, and Compound 4 were dissolved in ethanol at a concentration of 1% (w/v) to prepare samples for application. Further, as a control, ethanol was used alone as a sample for application.

On day 15 of the test, application of the samples was started. The respective samples were applied to the predetermined test sites once a day in an amount of 30 μL, and the application was continued for 6 weeks (until day 56 of the test).

On the day of the start of application (day 15 of the test) and after the completion of application for 6 weeks (on day 57 of the test), the skin brightness (L* value) of each of the test sites was measured using a colorimeter (CR-200, Konica Minolta Holdings, Inc.), and a ΔL* value was calculated by subtracting an L* value on day 15 of the test from an L* value on day 57 of the test. Table 4 shows the results. As degree of the pigmentation becomes stronger, the L* value becomes smaller. Therefore, it can be evaluated that, as the ΔL* value becomes larger, pigmentation is more inhibited.

TABLE 4

| Test sample | Concentration | ΔL* value |
|---|---|---|
| control | — | 2.0 ± 0.56 |
| Compound 2 | 1% | 3.9 ± 0.94 |
| Compound 3 | 1% | 3.9 ± 0.52 |
| Compound 4 | 1% | 3.4 ± 0.8 |

*The ΔL* value shows a mean ± standard deviation of eight animals.

The results shown in Table 4 reveal that, when Compound 2, Compound 3, and Compound 4 were applied to the skin at a concentration of 1%, all of them obviously inhibited pigmentation induced by ultraviolet rays.

Test Example 5

Measurement of Antimycotic Activity

The antimycotic activities of Compound 5 and clotrimazole known as an antimycotic were measured by the following method.

10.4 g of RPMI1640 (manufactured by SAFC Biosciences) were dissolved in 900 mL of distilled water, and 34.53 g of a 0.165 M MOPS buffer (manufactured by DOJINDO LABORATORIES) were added and dissolved by stirring. The mixture was adjusted to pH 7.0 with 10 N NaOH, and distilled water was added so that the mixture had a volume of 1 L. Then, the mixture was sterilized by filtration and used as RPMI1640 medium.

Dermatophytes (*Trichopyton mentagrophytes* (ATCC18748)) were inoculated into a 1/10 Sabouraud Dextrose agar medium (manufactured by DIFCO) and cultured at 28° C. for 14 days, and then a conidial suspension was prepared using 0.1% Tween80-including physiological saline. The suspension was filtered through gauze, and the number of the conidia was counted using a hemocytometer and then adjusted to $2.5 \times 10^5$/mL with the RPMI1640 medium. The resultant suspension was used as an inoculum.

Compound 5 and clotrimazole were diluted with the RPMI1640 medium to prepare 0.3125, 0.625, 1.25, 2.5, 5, 10, 20, and 200 µg/mL diluted solutions. The diluted solutions having different concentrations were dispensed into a 96-well flat-bottom microplate in an amount of 100 µL per well, and 80 µL of the inoculum and 20 µL of an Alamar Blue solution (manufactured by Nalgene) were further added thereto. Further, 80 µL of the inoculum and 20 µL of the Alamar Blue solution were added to 100 µL of the RPMI1640 medium in growth control wells, and 20 µL of the Alamar Blue solution was added to 180 µL of the RPMI1640 medium in negative control wells. The microplate was placed in a chamber in which the humidity was kept constant, and culture was started at 27° C., and the cells were observed every 24 hours. 120 hours from beginning of culture, i.e., when the growth control became obviously red (reduced form), absorbance measurement at 570 nm was performed using a microplate reader (SPECTRAMAX 250, manufactured by Molecular Device).

The test compounds were tested at the respective concentrations in triplicate. The growth inhibition rate (%) of each of the test compound-added groups was determined by the following equation based on a value calculated by subtracting an average absorbance value of the negative control from an average absorbance value of the growth control and the test compound-added wells. Further, $MIC_H$ (minimum inhibitory concentration; the minimum concentration at which the growth inhibition rate is 80% or more) was calculated from the growth inhibition rate of each test compound.

Growth inhibition rate (%)=[1−(average absorbance value in test compound-added wells−average absorbance value of negative control)/(average absorbance value of growth control−average absorbance value of negative control)]×100

Table 5 shows the results. Although $MIC_{80}$ of clotrimazole as an antimycotic was found to be 0.6250 µg/mL, $MIC_{80}$ of Compound 5 was not able to be calculated because Compound 5 did not inhibit the growth of *Trichopyton mentagrophytes* when Compound 5 was added at a concentration of 100 µg/mL, which was 100 times or more the concentration of clotrimazole. The results reveal that Compound 5 has no antimycotic activity. Therefore, the melanin production inhibitor of the present invention was found to be highly safe.

TABLE 5

| Concentration (µg/mL) | Growth inhibition rate (%) | |
|---|---|---|
| | Clotrimazole | Compound 5 |
| 0.1563 | 27.0 | −4.5 |
| 0.3125 | 53.0 | 8.0 |
| 0.6250 | 82.5 | −2.7 |
| 1.2500 | 92.2 | 3.1 |
| 2.5000 | 93.4 | −4.5 |
| 5.0000 | 85.4 | −17.5 |
| 10.0000 | 92.2 | −14.4 |
| 100.0000 | 88.9 | 13.2 |

Test Example 6

Measurement of Antimycotic Activity

The antimycotic activities of Compound 1, Compounds 3 to 6, Compound 40, Compound 41, triphenylmethylamine (Wako Pure Chemical Industries, Ltd.), triphenylmethanol (Wako Pure Chemical Industries, Ltd.), triphenylmethane (Wako Pure Chemical Industries, Ltd.), aminodiphenylmethane (Tokyo Chemical Industry Co., Ltd.), and clotrimazole known as an antimycotic were measured in the same procedure as in Test Example 5.

10.4 g of RPMI1640 (manufactured by SAFC Biosciences) were dissolved in 900 mL of distilled water, and 34.53 g of a 0.165 M MOPS buffer (manufactured by DOJINDO LABORATORIES) were added and dissolved by stirring. The mixture was adjusted to pH 7.0 with 10 N NaOH, and distilled water was added so that the mixture had a volume of 1 L. Then, the mixture was sterilized by filtration and used as RPMI1640 medium.

Dermatophytes (*Trichopyton mentagrophytes* (ATCC18748)) were inoculated into a 1/10 Sabouraud Dextrose agar medium (manufactured by DIFCO) and cultured at 28° C. for 14 days, and then a conidial suspension was prepared using 0.1% Tween80-including physiological saline. The suspension was filtered through gauze, and the number of the conidia was counted using a hemocytometer and then adjusted to $2.5 \times 10^5$/mL with the RPMI1640 medium. The resultant suspension was used as an inoculum.

Compound 1, Compounds 3 to 6, Compound 40, Compound 41, triphenylmethylamine, triphenylmethanol, triphenylmethane, aminodiphenylmethane, and clotrimazole were diluted with the RPMI1640 medium to prepare 0.3125, 0.625, 1.25, 2.5, 5, 10, 20, and 200 µg/mL diluted solutions. The diluted solutions having different concentrations were dispensed into a 96-well flat-bottom microplate in an amount of 100 µl, per well, and 80 µL of the inoculum and 20 µl, of an Alamar Blue solution (manufactured by Nalgene) were further added thereto. Further, 80 µl, of the inoculum and 20 µl, of the Alamar Blue solution were added to 100 µL of the RPMI1640 medium in growth control wells, and 20 µL of the Alamar Blue solution was added to 180 µL of the RPMI1640 medium in negative control wells. The microplate was placed in a chamber in which the humidity was kept constant, and then culture was started at 27° C., and the cells were observed every 24 hours. 120 hours from beginning of culture, i.e., when the growth control became obviously red (reduced form), absorbance measurement at 570 nm was performed using a microplate reader (SPECTRAMAX 250, manufactured by Molecular Device).

The test compounds were tested at the respective concentrations in triplicate. The growth inhibition rate (%) of each of the test compound-added groups was determined by the following equation based on a value calculated by subtracting an average absorbance value of the negative control from an average absorbance value of the growth control and the test compound-added wells. Further, $MIC_{80}$ (minimum inhibitory concentration; the minimum concentration at which the growth inhibition rate is 80% or more) was calculated from the growth inhibition rate of each test compound.

Growth inhibition rate (%)=[1−(average absorbance value in test compound-added wells-average absorbance value of negative control)/(average absorbance value of growth control-average absorbance value of negative control)]×100

Table 6 shows the results. $MIC_{80}$ of clotrimazole as an antimycotic was found to be 0.6250 μg/mL. Further, $MIC_{80}$ values of compounds having an imidazole skeleton, i.e. Compound 1, Compound 40, and Compound 41 were found to be 0.6250 μg/mL, 10.0000 μg/mL, and 5.0000 μg/mL, respectively. On the other hand, the compounds each having no imidazole skeleton were found to have an $MIC_{80}$ value of 100 μg/mL, which was 100 times or more that of clotrimazole (Compound 4, Compound 14, and triphenylmethanol) or have no growth inhibitory effect on *Trichopyton mentagrophytes* even when the compounds were added at a concentration of 100 μg/mL (Compound 3, Compound 5, Compound 6, triphenylmethylamine, triphenylmethane, and aminodiphenylmethane), and it was impossible to calculate $MIC_{80}$ values. The results reveal that compounds each having no imidazole skeleton have no antimycotic activity. Therefore, the melanin production inhibitor of the present invention was found to be highly safe. Further, the inhibitory effect on melanin production of the melanin production inhibitor of the present invention was considered not to be provided by an antimycotic activity.

TABLE 6

| Component added to medium | $MIC_{80}$ Concentration (μg/mL) |
| --- | --- |
| Clotrimazole | 0.6250 |
| Compound 1 | 0.6250 |
| Compound 40 | 10.0000 |
| Compound 41 | 5.0000 |
| Compound 3 | >100.0000 |
| Compound 4 | 100.0000 |
| Compound 5 | >100.0000 |
| Compound 6 | >100.0000 |
| Compound 14 | 100.0000 |
| Triphenylmethylamine | >100.0000 |
| Triphenylmethanol | 100.0000 |
| Triphenylmethane | >100.0000 |
| Aminodiphenylmethane | >100.0000 |

Test Example 7

Tyrosinase Activity Measurement Test Using Cultured Normal Human Melanocytes (1) Preparation of Protein Solution Normal human melanocytes (manufactured by Kurabo Industries Ltd.) prepared at $4×10^5$ cells/4 mL with complete medium for culture of melanocytes (manufactured by Kurabo Industries Ltd.) were seeded into 42 dishes with a diameter of 6 cm in an amount of 4 mL per dish and cultured in a 5% carbon dioxide atmosphere at 37° C. for 24 hours.

The concentrations of Compound 1, Compounds 3 to 6, Compound 40, Compound 41, triphenylmethylamine (Wako Pure Chemical Industries, Ltd.), triphenylmethanol (Wako Pure Chemical Industries, Ltd.), triphenylmethane (Wako Pure Chemical Industries, Ltd.), and aminodiphenylmethane (Wako Pure Chemical Industries, Ltd.) were prepared at 2.0 mM to 50 mM with dimethylsulfoxide (DMSO, Wako Pure Chemical Industries, Ltd.), and 15 μL of each of the solutions were mixed in 15 mL of the complete medium for culture of melanocytes to prepare medium each including 2.0 μM to 50 μM of the compounds. In addition, complete medium for culture of melanocytes including 0.1% DMSO was prepared as a control.

Thereafter, the medium in all the dishes was exchanged under the following conditions. Specifically, 4 mL per dish of fresh medium for culture of melanocytes each including 0.1% DMSO (control) was added to three dishes, and 4 mL per dish of medium adjusted so as to include 2.0 μM to 50 μM compounds was added to the other 39 dishes including three dishes for each concentration. Then, the cells were cultured for further 3 days under the same conditions as the above. After the completion of culture, the culture medium was removed from the respective wells, and the cells were washed with phosphate buffered physiological saline (PBS) and then separated from the bottoms of the wells with medium including trypsin and EDTA to prepare cell suspensions, followed by centrifugation to collect the cells. The collected cells were suspended in phosphate buffered physiological saline (PBS) and collected by centrifugation. This operation was repeated twice to wash cells.

A protein extraction solution (0.5% IGEPAL•CA-630 (manufactured by Sigma-Aldrich Co.), 0.005% sodium dodecyl sulfate (manufactured by Wako Pure Chemical Industries, Ltd.), 0.025% deoxycholic acid (manufactured by Sigma-Aldrich Co.), $1×10^{-1}$% protease inhibitor cocktail (manufactured by Sigma-Aldrich Co.), and a 50 mM sodium phosphate buffer (pH 6.8)) were added to the collected cells, and the suspensions were stirred for several minutes and left to stand-still on ice for 30 minutes. Centrifugation was performed to separate the supernatants and precipitates, and the supernatants were collected and then appropriately diluted with the protein extraction solution to prepare 15 μg/20 μL protein solutions.

(2) Measurement of Tyrosinase Activity 3-(3,4-Dihydroxyphenyl)-L-alanine (L-DOPA, manufactured by Wako Pure Chemical Industries, Ltd.) was dissolved in a 50 mM sodium phosphate buffer (pH 6.8) to prepare a 0.1% L-DOPA solution (a solution of a substrate of tyrosinase).

The protein solution prepared by the above-mentioned method was heated to 37° C. and then added to a 96-well plate in an amount of 20 μL per well, and the 0.1% L-DOPA solution heated to 37° C. in the same way as above was added in an amount of 180 μL per well, followed by measurement of absorbance at 405 nm for 5 minutes at 37° C. using a plate reader (Novapath 680, manufactured by Bio-Rad).

The test compounds were tested at the respective concentrations in triplicate. The average absorbance value of the protein solution collected from test compound-free cells (control) was defined as 100%, and the rate of an absorbance of a protein solution collected from test compound-added cells (%) was determined by the following equation and calculated as a tyrosinase activity.

Tyrosinase activity (%)=(absorbance in well to which protein solution collected from test compound-added cells was added)/(average absorbance value in well to which control protein solution was added)×100

It should be noted that the tyrosinase activity measured here is estimated to be proportional to the expression amount of tyrosinase protein in normal human melanocytes. It is considered that, in the case where the tyrosinase activity is small, the expression of tyrosinase protein is inhibited (including the inhibition of the maturation of the immature tyrosinase protein).

Table 7 shows the results. Further, the results of melanin production inhibition by treatment with the respective test compounds, determined in the same procedure as in Test Example 1, are also shown in the table.

Amounts of the melanin production when the cells were treated with 2.5 µM clotrimazole as an antimycotic was 23.2% of that of the control, and inhibitory effect on melanin production was observed. Further, the tyrosinase activity of the protein extracted from the cells treated with the same concentration of clotrimazole was 13.5% of that of the control, and the inhibitory effect on melanin production of clotrimazole was considered to be provided by the inhibitory effect on the expression level of tyrosinase protein. On the other hand, in the cases of Compounds 3 to 6 and 14, the amounts of melanin were about 20 to 30% of that of the control, and the compounds were found to inhibit melanin production. However, the tyrosinase activities when the cells were treated with the same concentration of the compounds were almost the same as that of the control, and the compounds were found to have no inhibitory effect on the expression level of tyrosinase protein. The results reveal that the inhibitory effects on melanin production of the compounds were considered to be provided by a mechanism other than inhibition of the expression level of tyrosinase protein.

TABLE 7

| Component added to medium | Treatment concentration (µM) | Amount of melanin* (%/control) | Tyrosinase activity** (%/control) |
| --- | --- | --- | --- |
| Clotrimazole | 2.5 | 23.2 ± 2.03 | 13.5 ± 0.77 |
| Compound 1 | 4 | 29.5 ± 2.50 | 20.3 ± 1.89 |
| Compound 40 | 20 | 44.7 ± 4.20 | 44.5 ± 5.78 |
| Compound 41 | 15 | 34.1 ± 2.58 | 12.4 ± 2.12 |
| Compound 3 | 10 | 22.3 ± 0.63 | 104.8 ± 3.87 |
| Compound 4 | 2 | 34.2 ± 3.58 | 96.0 ± 5.49 |
| Compound 5 | 4 | 16.8 ± 0.96 | 106.6 ± 4.14 |
| Compound 6 | 4 | 17.2 ± 0.80 | 99.6 ± 3.31 |
| Compound 14 | 40 | 37.9 ± 1.39 | 101.6 ± 3.86 |
| Triphenylmethylamine | 20 | 23.0 ± 2.41 | 104.2 ± 5.72 |
| Triphenylmethanol | 15 | 31.6 ± 2.39 | 108.6 ± 9.11 |
| Triphenylmethane | 15 | 32.2 ± 1.82 | 99.8 ± 7.94 |
| Aminodiphenylmethane | 50 | 28.8 ± 2.03 | 103.3 ± 7.82 |

*The rate when the average radioactivity of the control is defined as 100% is shown as the amount of melanin, which shows a mean ± standard deviation of three samples.
**The rate when the average absorbance of the control is defined as 100% is shown as the tyrosinase activity, which shows a mean ± standard deviation of three samples.

<Production Example of External Preparation for Skin>

According to the formulation shown in Table 8, a cosmetic (lotion) was prepared as the external preparation for skin of the present invention. Specifically, the components of the formulation were heated to 80° C., stirred, dissolved, and cooled by stirring, to obtain Lotion 1. In the same way as above, a lotion of Comparative Example 1 was prepared by replacing Compound 2 with water, and a lotion of Comparative Example 2 was prepared by replacing Compound 2 with arbutin.

TABLE 8

| Component | w/w % |
| --- | --- |
| Compound 2 | 1 |
| POE (60) cured castor oil | 0.1 |
| 1,3-Butanediol | 5 |
| Glycerin | 2 |

TABLE 8-continued

| Component | w/w % |
| --- | --- |
| Polyethylene glycol 400 | 3 |
| 1,2-Pentanediol | 3 |
| Xanthane gum | 0.1 |
| Water | 85.8 |
| Total | 100 |

Test Example 8

Inhibitory Effect of Compound 2 on Ultraviolet Ray-Induced Pigmentation in Human Inhibitory effects on pigmentation of Lotion 1 and the cosmetics of Comparative Example 1 and Comparative Example 2 were examined. Two sites each having a size of 1.5 cm×1.5 cm, which were divided into two-tiered sections respectively, were set at the medial side of the upper arm of each volunteer panelist so as to specify a total of four sites. The sites were irradiated with ultraviolet rays at a minimum erythema dose (1 MED) once a day for 3 consecutive days, i.e., 3 times. From the first day after the completion of irradiation, 50 µL of each sample were applied thereto once a day for 28 consecutive days. One site was not treated. 24 hours after the completion of application, the skin brightness (L* value) of each test site was measured using a colorimeter (CR-300, Konica Minolta Holdings, Inc.), and a ΔL* value was calculated based on an L value of the untreated site. Table 9 shows the results. As degree of the pigmentation becomes stronger, the L* value becomes smaller. Therefore, it can be evaluated that, as the ΔL* value becomes larger, pigmentation is more inhibited. The fact suggests that the cosmetic which is the external preparation for skin of the present invention has an excellent pigmentation inhibitory effect. This is considered to be provided by the inhibitory effect on melanin production of Compound 2 described above.

TABLE 9

| Test sample | ΔL* value |
| --- | --- |
| Lotion 1 | 1.42 |
| Comparative Example 1 | 0.11 |
| Comparative Example 2 | 0.62 |

Test Example 9

Inhibitory Effects of Other Compounds on Ultraviolet Ray-Induced Pigmentation in Human Lotions 2 to 6 including Compounds 1, 3, 4 to 6, respectively, were prepared in the same way as in the case of Lotion 1, and the pigmentation inhibitory effects were examined in the same way as in Test Example 8. Table 10 shows the results. All the lotions were found to have excellent pigmentation inhibitory effects.

TABLE 10

| Test sample | ΔL* value |
| --- | --- |
| Lotion 2 (Compound 1) | 1.37 |
| Lotion 3 (Compound 3) | 1.28 |
| Lotion 4 (Compound 4) | 1.20 |

53

TABLE 10-continued

| Test sample | ΔL* value |
|---|---|
| Lotion 5 (Compound 5) | 1.18 |
| Lotion 6 (Compound 6) | 1.32 |

<Production Example 2 of External Preparation for Skin>

According to the formulation shown in Table 11, a cosmetic as an external composition for skin of the present invention (Milky liquid 1) was prepared. Specifically, the components A, B, and C were heated to 80° C., and the component C was gradually added to the component B with stirring to neutralize the solution, and the component C was gradually added with stirring, followed by homogenization of emulsified particles using a homomixer, to obtain a milky liquid. In the same way as above, a milky liquid of Comparative Example 3 was prepared by replacing Compound 2 with water.

TABLE 11

| | Component | Part(s) by weight |
|---|---|---|
| A | Cetyl 2-ethylhexanoate | 15 |
| | Sorbitan monostearate | 0.3 |
| | Selachyl alcohol | 0.5 |
| | Compound 2 | 1 |
| B | 1,3-Butanediol | 8 |
| | Glycerin | 2 |
| | Xanthane gum | 0.1 |
| | Pemulen TR-2 | 0.2 |
| | (Acrylic acid-alkyl methacrylate copolymer) | |
| | Methylparaben | 0.2 |
| | Water | 42.6 |
| C | Potassium hydroxide | 0.1 |
| | Water | 30 |
| | Total | 100 |

Test Example 10

Inhibitory Effect of Compound 2 on Ultraviolet Ray-Induced Pigmentation in Human The pigmentation inhibitory effect of Compound 2 was examined using Milky liquid 1 and the cosmetic of Comparative Example 3. On the first day of the test, two sites each having a size of 1.5 cm×1.5 cm were set at the medial side of the upper arm of each volunteer panelist, and the skin brightness (L* value) of each test site was measured using a colorimeter (CR-300, Konica Minolta Holdings, Inc.). After the measurement of the skin brightness, from the first day of the test, the test sites were irradiated with ultraviolet rays at a minimum erythema dose (1 MED) once a day for 3 consecutive days, i.e., 3 times in total. From the day immediately after the completion of the third ultraviolet ray irradiation, 50 μL of each sample were applied 3 times a day for 28 consecutive days. 24 hours after the completion of application, the skin brightness (L* value) in each test site was measured using a colorimeter (CR-300, Konica Minolta Holdings, Inc.), and a ΔL* value was calculated based on an L value on the first day of the test. As degree of the pigmentation becomes stronger, the L* value becomes smaller. Therefore, it can be evaluated that, as the ΔL* value becomes larger, pigmentation is more inhibited. Table 12 shows the results. The results suggest that Milky liquid 1 which is the external preparation for skin of the present invention has an excellent pigmentation inhibitory effect. This is considered to be provided by the inhibitory effect on melanin production of Compound 2 described above.

54

TABLE 12

| Test sample | ΔL* value |
|---|---|
| Milky liquid 1 | −2.74 |
| Comparative Example 3 | −3.54 |

INDUSTRIAL APPLICABILITY

The present invention can be applied to an external preparation for skin such as a skin-whitening cosmetic.

What is claimed is:

1. A topically applied cosmetic composition for the inhibition of melanin production, comprising a compound of general formula (5):

(5)

wherein A4, A5, and A6 are each independently selected from the group consisting of phenyl and pyridyl which may be substituted by methyl, methoxy, or hydroxyl;

R13 and R14 are bound to each other to form, together with a nitrogen atom represented by N, a saturated heterocyclic ring which has 4 or 5 carbon atoms and may be substituted by hydroxyl or oxo;

wherein the compound of general formula (5) is present in an amount from 0.001 w/w % to 10 w/w % in the topical cosmetic composition; and wherein the topical cosmetic composition excludes clotrimazole.

2. The composition according to claim 1, wherein the compound is selected from the group consisting of 1-(triphenylmethyl)piperidine (Compound 5) and 1-(triphenylmethyl)pyrrolidine (Compound 6)

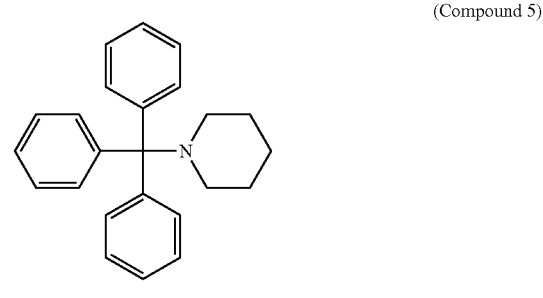

(Compound 5)

1-(Triphenylmethyl)piperidine

-continued
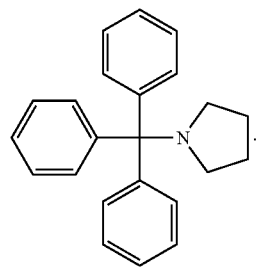
1-(Triphenylmethyl)pyrrolidine
(Compound 6)
* * * * *

UNITED STATES PATENT AND TRADEMARK OFFICE
CERTIFICATE OF CORRECTION

| | |
|---|---|
| PATENT NO. | : 8,846,012 B2 |
| APPLICATION NO. | : 13/131827 |
| DATED | : September 30, 2014 |
| INVENTOR(S) | : Kouji Yokoyama et al. |

It is certified that error appears in the above-identified patent and that said Letters Patent is hereby corrected as shown below:

On the Title Page

In column 2 (page 2, item 56) at line 7, Under Other Publications, change "Aulenoorf," to --Aulendorf,--.

In column 2 (page 2, item 56) at line 9, Under Other Publications, change "Triphenyimethylmorpholine" to --Triphenylmethylmorpholine--.

In column 2 (page 2, item 56) at line 12, Under Other Publications, change "Pregamon" to --Pergamon--.

In the Specification

In column 15 at line 13, Change "ibota wax," to --ibotta wax,--.

In column 17 at line 34 (approx.), Change "an hydrous" to --anhydrous--.

In column 17 at line 36 (approx.), Change "of funder" to --off under--.

In column 24 at line 54, Change ">1000)." to -->100%).--.

In column 25 at line 42 (approx.), Change "ltd.)" to --Ltd.)--.

In column 25 at line 44 (approx.), Change "62.10" to --δ2.10--.

In column 26 at line 64, Change "δ 3.80" to --δ3.80--.

In column 45 at line 53 (approx.), Change "concentrations," to --concentrations--.

In column 47 at line 16, Change "(Trichopyton" to --(Trichophyton--.

In column 47 at line 49, Change "$MIC_H$" to --$MIC_{80}$--.

In column 47 at line 62, Change "Trichopyton" to --Trichophyton--.

In column 48 at line 35, Change "(Trichopyton" to --(Trichophyton--.

In column 49 at line 22, Change "Trichopyton" to --Trichophyton--.

In column 50 at lines 34-35, Change "standstill" to --stand still--.

Signed and Sealed this
Twenty-sixth Day of May, 2015

Michelle K. Lee
*Director of the United States Patent and Trademark Office*

In column 50 at line 52, Change "(Novapath 680," to --(Novopath 680,--.

In column 52 at line 6 (Table 8-continued), Change "Xanthane" to --Xanthan--.

In column 53 at line 29 (approx., Table 11), Change "Xanthane" to --Xanthan--.